US012285565B2

United States Patent
Dwyer et al.

(10) Patent No.: US 12,285,565 B2
(45) Date of Patent: Apr. 29, 2025

(54) SELF-SEALING RESPIRATORY FILTER AND CONDENSATE MANAGEMENT APPARATUS

(71) Applicant: TELEFLEX MEDICAL INCORPORATED, Morrisville, NC (US)

(72) Inventors: Daniel P. Dwyer, Cary, NC (US); Christopher S. Jackson, Raleigh, NC (US)

(73) Assignee: TELEFLEX MEDICAL INCORPORATED, Morrisville, NC (US)

( * ) Notice: Subject to any disclaimer, the term of this patent is extended or adjusted under 35 U.S.C. 154(b) by 826 days.

(21) Appl. No.: 17/407,649

(22) Filed: Aug. 20, 2021

(65) Prior Publication Data

US 2022/0054787 A1 Feb. 24, 2022

Related U.S. Application Data

(60) Provisional application No. 63/069,337, filed on Aug. 24, 2020.

(51) Int. Cl.
*A61M 16/08* (2006.01)
*A61M 16/10* (2006.01)
(Continued)

(52) U.S. Cl.
CPC ...... *A61M 16/0808* (2013.01); *A61M 16/106* (2014.02); *B01D 46/0031* (2013.01);
(Continued)

(58) Field of Classification Search
CPC ............ A61M 16/0808; A61M 16/106; A61M 2205/7536; B01D 46/0031;
(Continued)

(56) References Cited

U.S. PATENT DOCUMENTS 2,195,565 A 4/1940 Fricke
3,556,097 A 1/1971 Wallace
(Continued)

FOREIGN PATENT DOCUMENTS

| CN | 108939245 A | * 12/2018 | ........ A61M 16/0808 |
| CN | 109621144 A | 4/2019 | |
| DE | 3643624 A1 | 8/1987 | |

OTHER PUBLICATIONS

CN 108939245 machine translation (Year: 2018).*

*Primary Examiner* — Timothy A Stanis
*Assistant Examiner* — Sara K Toich
(74) *Attorney, Agent, or Firm* — BakerHostetler

(57) ABSTRACT

A respiratory filter and condensate management apparatus is provided for use in a breathing circuit during patient respiration. The apparatus includes a filter housing having an air inlet port and an air outlet port. A filter member is provided within the filter housing and located in an expiratory air flow path. A collection jar is removably attached to the filter housing and has a liquid reservoir to collect liquid formed by condensation in the flow of expiratory air within the filter housing when the collection jar is attached to the filter housing. A valve assembly moves to an open position when the filter housing is attached to the collection jar to allow drainage of the liquid from the filter housing. The valve assembly moves to a closed position when the filter housing is detached from the collection jar to prevent drainage of the liquid from the filter housing.

20 Claims, 10 Drawing Sheets

(51) Int. Cl.
*B01D 46/00* (2022.01)
*B01D 46/42* (2006.01)
*B01D 46/52* (2006.01)

(52) U.S. Cl.
CPC ..... *B01D 46/0032* (2013.01); *B01D 46/4272* (2013.01); *B01D 46/521* (2013.01); *A61M 2205/7536* (2013.01)

(58) Field of Classification Search
CPC ..... Y10T 137/86196; Y10T 137/87957; F16L 37/26; F24F 3/14; F24F 1/02; F24F 1/035; F24F 1/04; F24F 1/0358; F24F 1/037; F24F 1/0083; F24F 1/0087; F24F 2003/144; F24F 2003/1446; F24F 2006/008; F28D 2021/0038
See application file for complete search history.

(56) References Cited

U.S. PATENT DOCUMENTS

| | | | |
|---|---|---|---|
| 3,798,879 A * | 3/1974 | Schmidt-Burbach | B03C 3/155 55/482 |
| 3,803,817 A | 4/1974 | Lewis | |
| 4,036,616 A | 7/1977 | Byrns | |
| 4,063,913 A | 12/1977 | Kippel et al. | |
| 4,133,656 A | 1/1979 | Kippel et al. | |
| 4,171,962 A | 10/1979 | Huston et al. | |
| 4,172,709 A | 10/1979 | Huston et al. | |
| 4,493,717 A | 1/1985 | Berger et al. | |
| 4,592,350 A | 6/1986 | Maryyanek et al. | |
| 4,696,687 A | 9/1987 | Billiet et al. | |
| 4,951,661 A * | 8/1990 | Sladek | A61M 16/0808 128/205.24 |
| 5,033,507 A | 7/1991 | Pouchot | |
| 5,035,236 A | 7/1991 | Kanegaonkar | |
| 5,052,385 A | 10/1991 | Sundstrom | |
| 5,158,077 A | 10/1992 | Sundstrom | |
| 5,186,165 A | 2/1993 | Swann | |
| 5,195,527 A | 3/1993 | Hicks | |
| 5,230,727 A | 7/1993 | Pound et al. | |
| 5,288,469 A | 2/1994 | Skalla | |
| 5,394,867 A | 3/1995 | Swann | |
| 5,423,892 A | 6/1995 | Kahlbaugh et al. | |
| 5,460,172 A | 10/1995 | Eckerbom et al. | |
| 5,478,377 A | 12/1995 | Scavnicky et al. | |
| 5,590,644 A | 1/1997 | Rosenkoetter | |
| 5,826,575 A * | 10/1998 | Lall | A61M 16/0808 128/205.27 |
| 5,992,413 A | 11/1999 | Martin et al. | |
| 6,095,135 A | 8/2000 | Clawson et al. | |
| 6,105,576 A | 8/2000 | Clawson et al. | |
| 6,146,449 A | 11/2000 | Lee et al. | |
| 6,179,890 B1 | 1/2001 | Ramos et al. | |
| 6,209,541 B1 | 4/2001 | Wallace | |
| 6,330,883 B1 | 12/2001 | Berger | |
| 6,355,076 B2 | 3/2002 | Gieseke et al. | |
| 6,363,930 B1 | 4/2002 | Clawson et al. | |
| 6,540,806 B2 | 4/2003 | Reinhold | |
| 6,550,476 B1 | 4/2003 | Ryder | |
| 6,702,880 B2 | 3/2004 | Roberts et al. | |
| 6,783,565 B2 | 8/2004 | Gieseke et al. | |
| 6,860,267 B2 | 3/2005 | Capon et al. | |
| 7,311,764 B2 | 12/2007 | Friday et al. | |
| 7,594,509 B2 | 9/2009 | Burk | |
| 7,921,846 B1 | 4/2011 | Marler et al. | |
| 8,033,131 B2 * | 10/2011 | Yoon | F24F 3/153 62/291 |
| 8,312,876 B2 | 11/2012 | Mutze et al. | |
| 8,561,606 B2 | 10/2013 | Korneff | |
| 8,869,796 B2 | 10/2014 | Wood | |
| 8,932,380 B2 | 1/2015 | Okada | |
| 9,095,675 B2 | 8/2015 | Stjernfelt et al. | |
| 9,209,541 B2 | 12/2015 | Miyazaki | |
| 9,352,268 B2 | 5/2016 | Fiet et al. | |
| 2003/0106555 A1 | 6/2003 | Tovey | |
| 2003/0234016 A1 | 12/2003 | Swann | |
| 2004/0118397 A1 | 6/2004 | Swann | |
| 2004/0123974 A1 | 7/2004 | Marler et al. | |
| 2004/0216743 A1 | 11/2004 | Orr et al. | |
| 2005/0121074 A1 * | 6/2005 | Pittaway | A61M 16/0808 137/171 |
| 2005/0155665 A1 | 7/2005 | Schlacchter | |
| 2005/0160911 A1 | 7/2005 | Friday et al. | |
| 2006/0278227 A1 | 12/2006 | Nguyen | |
| 2010/0122702 A1 * | 5/2010 | Reinboth | A61M 16/0808 128/205.27 |
| 2010/0313532 A1 * | 12/2010 | Stjernfelt | B01D 46/0002 55/482 |
| 2010/0319699 A1 | 12/2010 | Wood | |
| 2012/0167889 A1 | 7/2012 | Friday et al. | |
| 2017/0021122 A1 | 1/2017 | Wisniewski | |

\* cited by examiner

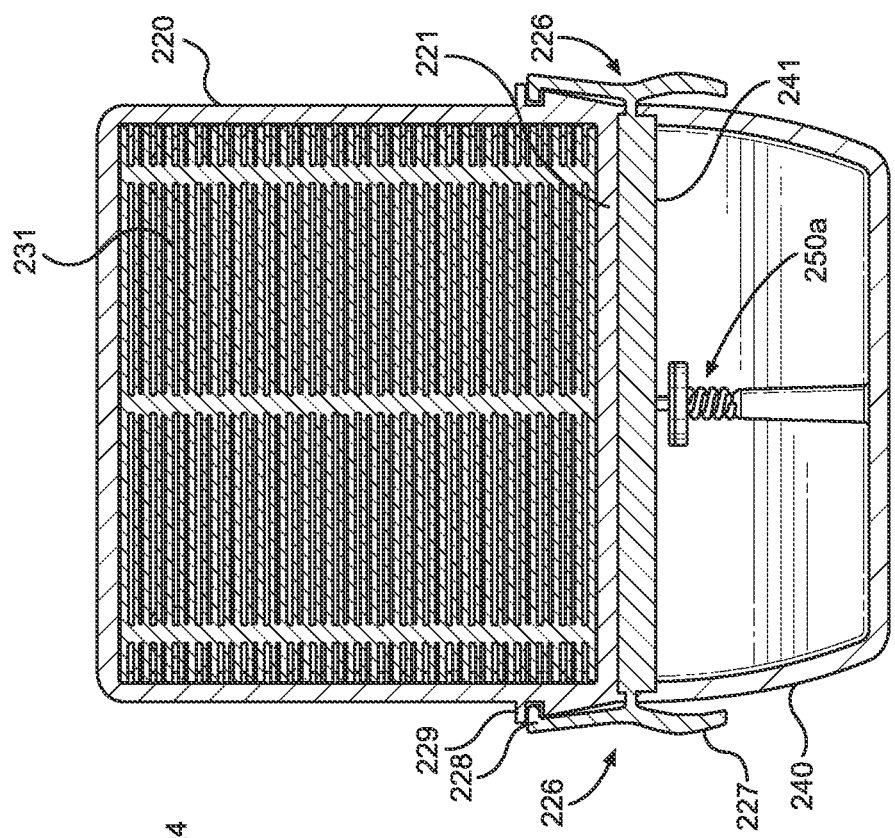
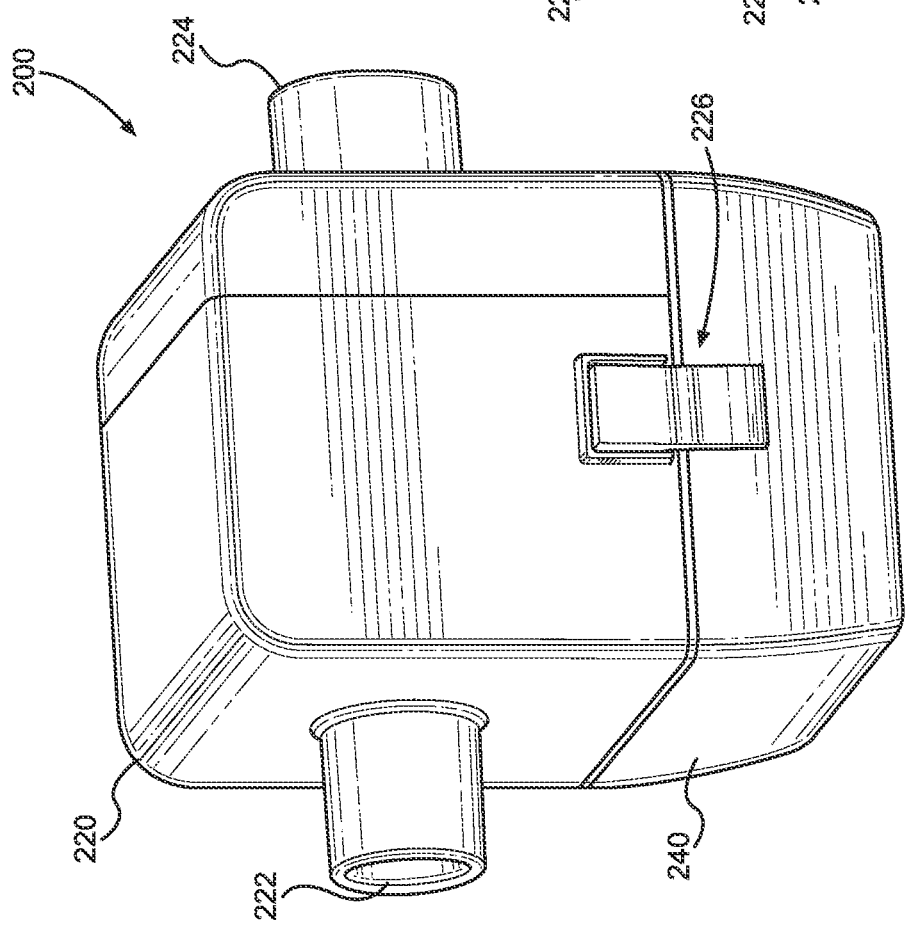
FIG. 7
FIG. 8

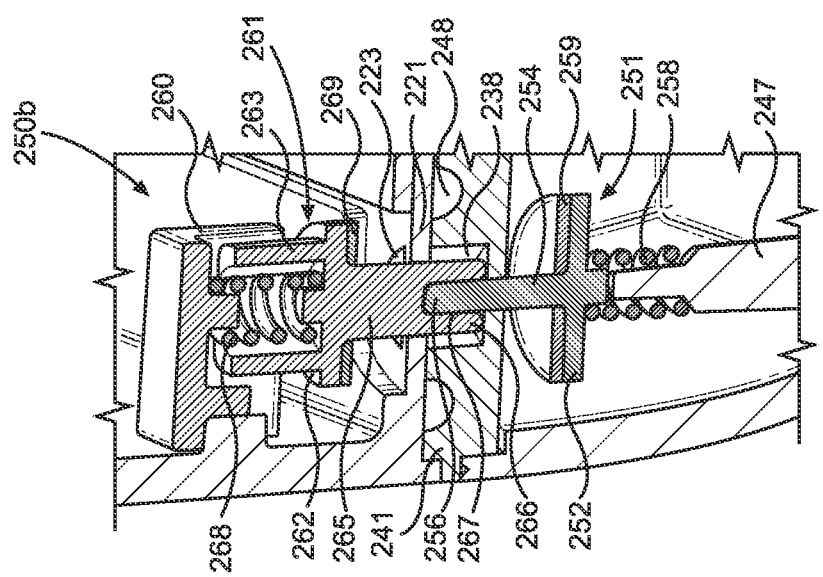
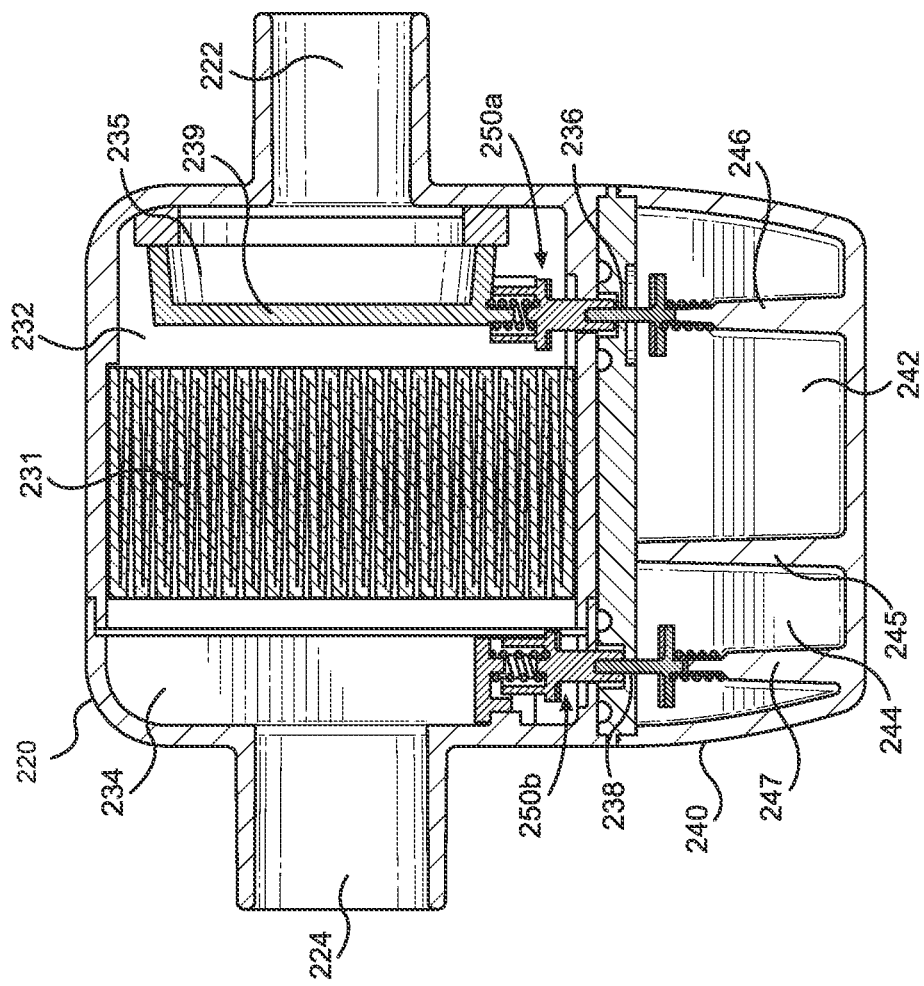

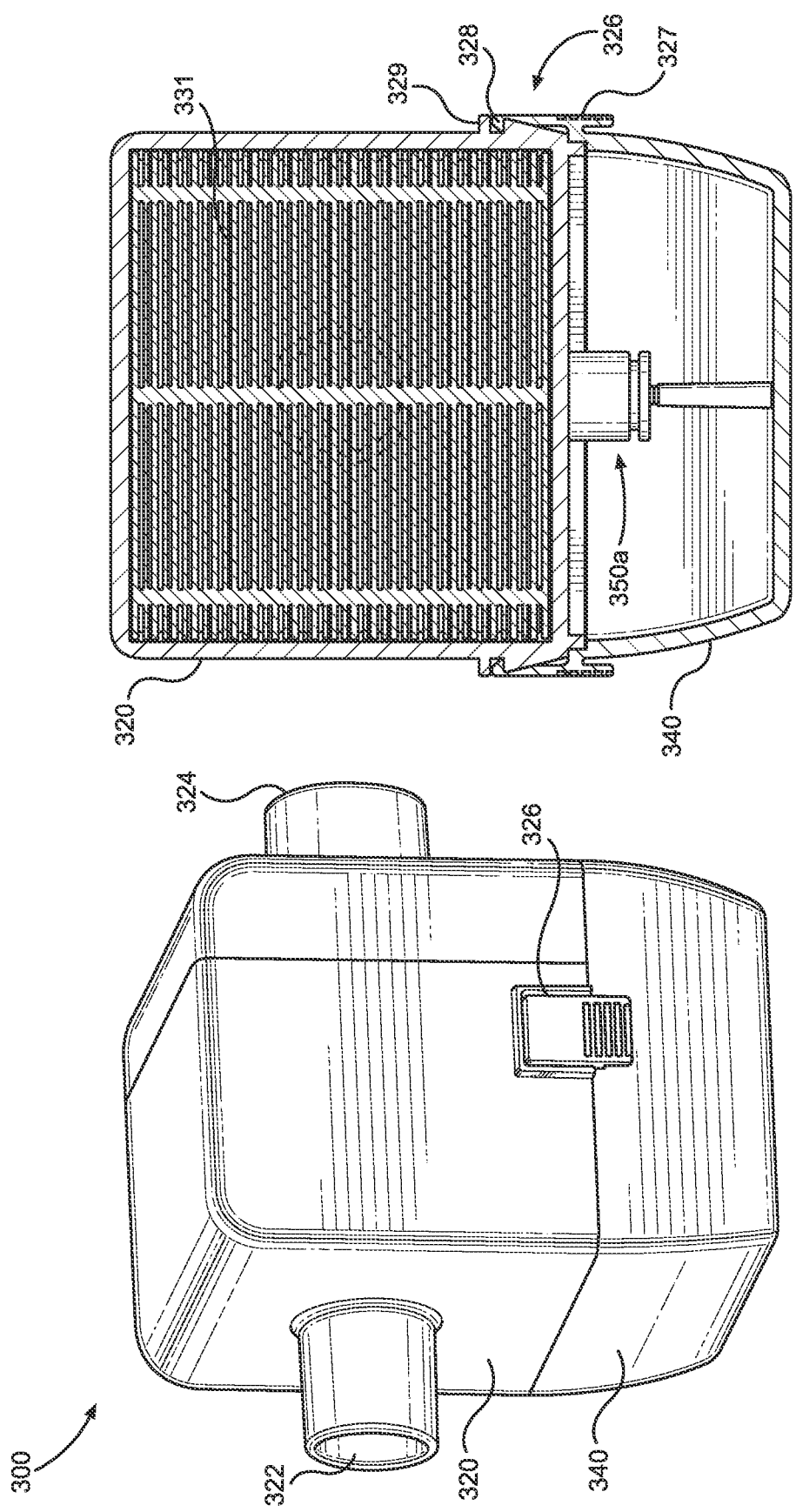

SELF-SEALING RESPIRATORY FILTER AND CONDENSATE MANAGEMENT APPARATUS

CROSS-REFERENCE TO RELATED APPLICATIONS

This application claims the benefit of priority to U.S. Provisional Patent Application No. 63/069,337 filed Aug. 24, 2020, the entire contents of which are incorporated herein by reference.

FIELD OF THE INVENTION

The present disclosure generally relates to respiratory filters for use in a breathing circuit, and more particularly, to respiratory filters operable to manage an accumulation of condensate produced during active humidification.

BACKGROUND

Ventilators are commonly used to aid or replace a patient's respiratory function. Such ventilators are typically connected to a breathing circuit having an inspiratory limb for delivering a flow of air from the ventilator to the patient for inhalation, and an expiratory limb for returning a flow of exhaled air from the patient back to the ventilator. The flow of air is often heated and humidified to increase patient comfort and compliance during respiration.

A respiratory filter may be used in the breathing circuit between the expiratory limb and the ventilator in order to prevent the ventilator from being contaminated by bacteria, viruses, and/or other waste material exhaled by the patient during respiration. The exhaled air from the patient contains vapor that may form condensate within the expiratory limb. Similarly, vapor that reaches the respiratory filter may form condensate within the filter. Some conventional expiratory limbs may be heated, such as by a heating wire, to reduce the amount of condensate within the expiratory limb. However, conventional respiratory filters are unheated, and are therefore exposed to room air that is often colder than the air inside the filter. Thus, unwanted condensation or rainout commonly occurs within the filter when the heated and humidified air enters the colder filter.

The accumulation of condensate within the respiratory filter can saturate the filter material causing it to perform less effectively. For instance, resistance to air flow in the filter material may increase as the filter material becomes more saturated with water. Additionally, condensate that forms in the filter may be contaminated with bacteria, viruses, and/or other waste material from the patient.

Some typical respiratory filters may include a container to collect moisture on the circuit side of the filter. However, such filters routinely fill up with water and require dismantling or breaking of the breathing circuit in order to drain the excess fluid from the filter. It is advantageous to avoid taking apart the breathing circuit during respiration in order to maintain a positive end expiratory pressure (PEEP) and minimize the risk of infection. Moreover, ventilation patterns can be affected when conventional respiratory filters fill up with liquid from condensation, which can cause false triggering on the ventilator. Furthermore, known heated filters either require a ventilator that has a heating capability, a standalone filter heater, or a powered humidifier, each of which blocks viewing of the filter and are also cost prohibitive.

Accordingly, there is a clear need for a respiratory filter with a releasably attachable liquid drainage jar having self-sealing capabilities for condensate management during active humidification. In particular, the respiratory filter and condensate management apparatus of the present disclosure mitigates the buildup of liquid within the expiratory filter, minimizes filter change-outs, helps maintain PEEP in the breathing circuit, and mitigates the risk of infection due to breaking of the circuit, among other advantages.

SUMMARY

The foregoing needs are met, to a great extent, by the present disclosure of a respiratory filter and condensate management apparatus discussed herein. The respiratory filter and condensate management apparatus may comprise a filter housing including an air inlet port, an air outlet port, a base, and a base drain, the air inlet port configured to receive a flow of expiratory air, and the air outlet port configured to output the flow of expiratory air; a filter member provided within the filter housing and located in a flow path of the expiratory air between the air inlet port and the air outlet port; a collection jar removably attached to the filter housing, the collection jar including a liquid reservoir, a spill cover, and a cover drain, the cover drain and the base drain forming a liquid passageway operable to provide fluid communication between the filter housing and the liquid reservoir when the collection jar is attached to the filter housing, and the liquid reservoir operable to collect liquid formed by condensation in the flow of expiratory air within the filter housing when the collection jar is attached to the filter housing; and a valve assembly configured to permit passage of the liquid formed by condensation in the flow of expiratory gas through the liquid passageway when the valve assembly is in an open position, and configured to prevent passage of the liquid through the liquid passageway when the valve assembly is in a closed position.

According to another aspect of the disclosure, the valve assembly is operable to automatically assume the open position when the filter housing is attached to the collection jar.

According to another aspect of the disclosure, the valve assembly is operable to automatically assume the closed position when the filter housing is detached from the collection jar.

According to another aspect of the disclosure, the valve assembly comprises a housing slide configured to close the base drain of the filter housing when the collection jar is detached from the filter housing.

According to another aspect of the disclosure, the valve assembly further comprises a housing slide biasing member configured to bias the housing slide toward the base drain.

According to another aspect of the disclosure, the valve assembly further comprises an elastomeric housing seal to provide a water-tight seal between the housing slide and the base drain when the valve assembly is in the closed position.

According to another aspect of the disclosure, the valve assembly comprises a jar slide configured to close the cover drain of the collection jar when the collection jar is detached from the filter housing.

According to another aspect of the disclosure, the valve assembly further comprises a jar slide biasing member configured to bias the jar slide toward the cover drain.

According to another aspect of the disclosure, the valve assembly further comprises an elastomeric jar seal to provide a water-tight seal between the jar slide and the cover drain when the valve assembly is in the closed position.

According to another aspect of the disclosure, a latch mechanism is configured to securely and releasably attach the filter housing to the collection jar.

According to another aspect of the disclosure, the latch mechanism is operable to permit detachment of the collection jar from the filter housing without disconnecting the filter housing from the breathing circuit.

According to another aspect of the disclosure, an impact pad is provided within the filter housing and operable to remove liquid from the flow of expiratory air.

According to another aspect of the disclosure, the impact pad is an electrostatic pad.

According to another aspect of the disclosure, the filter member is pleated.

According to another aspect of the disclosure, the respiratory filter and condensate management apparatus for a breathing circuit may comprise a filter housing including a patient end and a ventilator end, the patient end having an air inlet port configured to receive a flow of expiratory air, and the ventilator end having an air outlet port configured to output the flow of expiratory air; a filter member provided within the filter housing and located in a flow path of the expiratory air between the air inlet port and the air outlet port; a collection jar removably attached to the filter housing, the collection jar including a patient end liquid reservoir operable to collect liquid formed by condensation in the flow of expiratory air within the filter housing when the collection jar is attached to the filter housing; and a patient end valve assembly configured to move to an open position when the filter housing is attached to the collection jar, and further configured to move to a closed position when the filter housing is detached from the collection jar.

According to another aspect of the disclosure, the filter housing further includes a base having a patient end base drain.

According to another aspect of the disclosure, the collection jar further includes a spill cover having a patient end cover drain, the patient end cover drain and the patient end base drain forming a patient end liquid passageway operable to provide fluid communication between the filter housing and the patient end liquid reservoir when the collection jar is attached to the filter housing.

According to another aspect of the disclosure, the patient end valve assembly is further configured to permit passage of the liquid formed by condensation in the flow of expiratory gas through the patient end liquid passageway when the patient end valve assembly is in an open position, and further configured to prevent passage of the liquid through the patient end liquid passageway when the patient end valve assembly is in a closed position.

According to another aspect of the disclosure, the collection jar further includes a ventilator end liquid reservoir operable to collect liquid formed by condensation in the flow of expiratory air within the filter housing when the collection jar is attached to the filter housing.

According to another aspect of the disclosure, a ventilator end valve assembly is configured to move to an open position when the filter housing is attached to the collection jar, and further configured to move to a closed position when the filter housing is detached from the collection jar.

There has thus been outlined certain embodiments of the disclosure in order that the detailed description thereof herein may be better understood, and in order that the present contribution to the art may be better appreciated. There are additional embodiments of the disclosure that will be described below and which form the subject matter of the claims appended hereto.

In this respect, before explaining at least one aspect of the respiratory filter and condensate management apparatus in detail, it is to be understood that the respiratory filter and condensate management apparatus is not limited in its application to the details of construction and to the arrangements of the components set forth in the following description or illustrated in the drawings. The respiratory filter and condensate management apparatus is capable of aspects in addition to those described, and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods, and systems for carrying out the several purposes of the respiratory filter and condensate management apparatus. It is important, therefore, that the claims be regarded as including such equivalent constructions insofar as they do not depart from the spirit and scope of the disclosure.

BRIEF DESCRIPTION OF THE DRAWINGS

In order that the disclosure may be readily understood, aspects of the respiratory filter and condensate management apparatus are illustrated by way of examples in the accompanying drawings, in which like parts are referred to with like reference numerals throughout.

FIG. 7 is a perspective view of a self-sealing respiratory filter and condensate management apparatus according to another implementation of the present disclosure.

FIG. 8 is a cross-sectional view from a side of the respiratory filter and condensate management apparatus of FIG. 7.

FIG. 9 is a cross-sectional view from a front of the respiratory filter and condensate management apparatus of FIG. 8.

FIG. 10*a* is a partial cross-sectional top perspective view of the ventilator-side valve assembly of the respiratory filter and condensate management apparatus of FIG. 9.

FIG. 12 is a perspective view of a self-sealing respiratory filter and condensate management apparatus according to another implementation of the present disclosure.

FIG. 13 is a cross-sectional view from a side of the apparatus depicted in FIG. 12.

DETAILED DESCRIPTION

Figure 2:
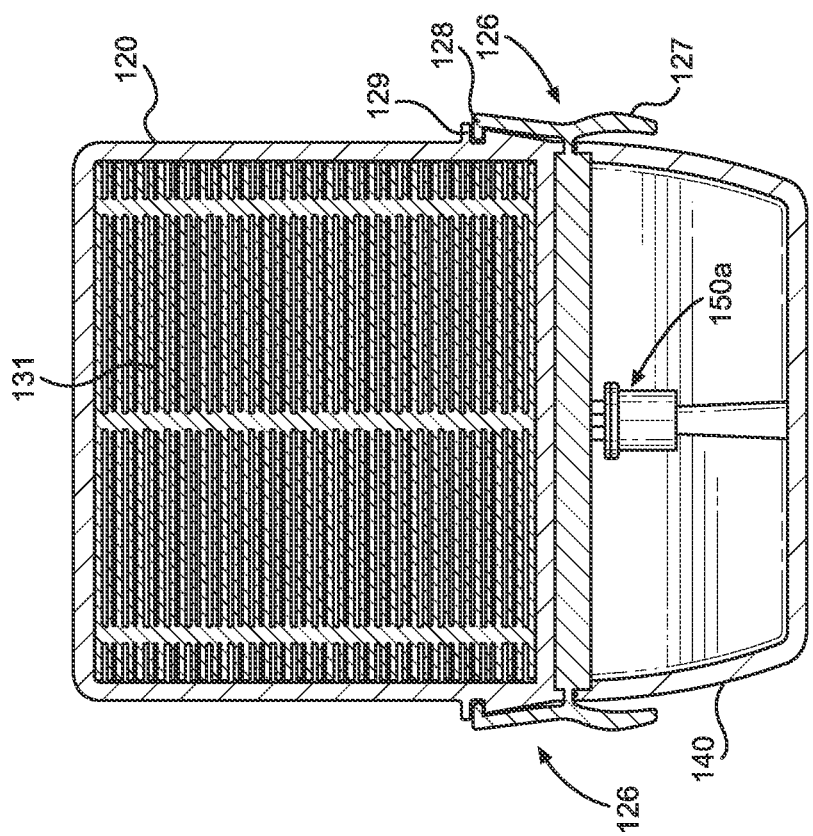
FIG. 2 is a cross-sectional side view of the respiratory filter and condensate management apparatus taken along line 2-2 of FIG. 1.
Figure 1:
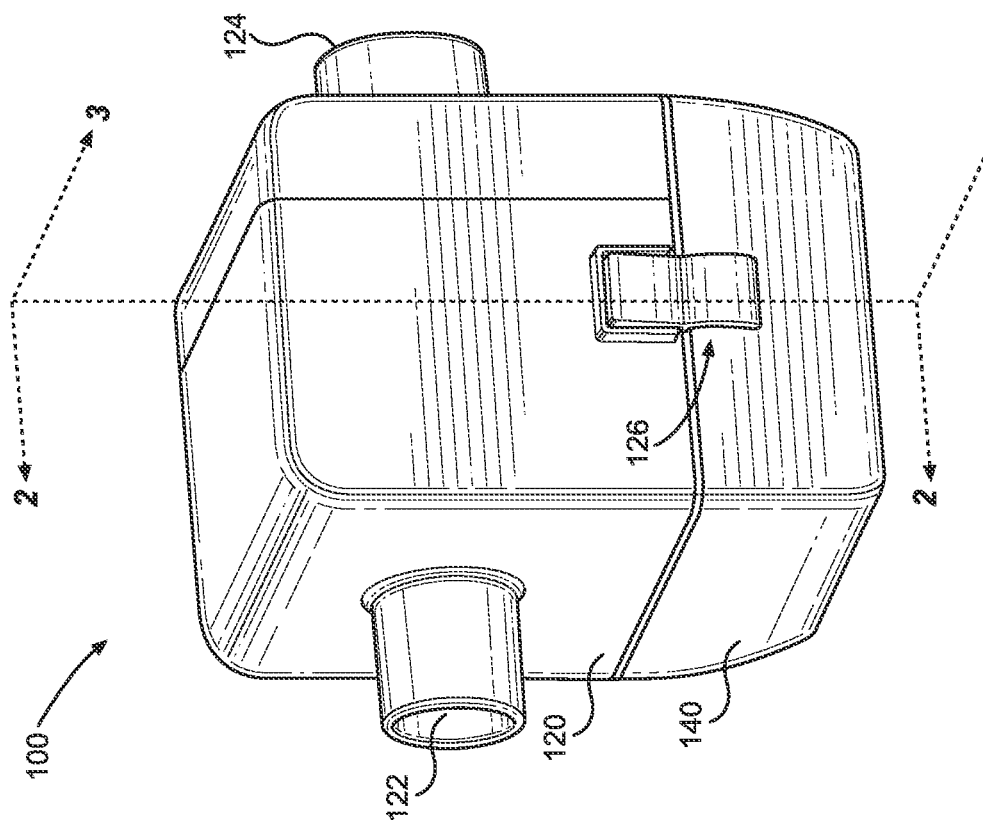
FIG. 1 is a perspective view of a self-sealing respiratory filter and condensate management apparatus for a breathing circuit according to an implementation of the present disclosure.

FIGS. 1-6 illustrate a self-sealing respiratory filter and condensate management apparatus 100 for a breathing circuit in accordance with an implementation of the present disclosure. The respiratory filter and condensate management apparatus 100 comprises a filter housing 120 and a collection jar 140. The collection jar 140 is releasably attachable to the filter housing 120. The filter housing 120 defines a filter compartment, and the collection jar 140 defines a condensate compartment. The filter housing 120 includes base 121, an air inlet port 122, and an air outlet port 124. The air inlet port 122 is configured to connect to an expiratory limb of the breathing circuit for receiving a flow of expiratory air, and the air outlet port 124 is configured to connect to a ventilator either directly or via a breathing circuit tubing for outputting the flow of expiratory air. A self-closing valve assembly 150a,b is provided to regulate passage of condensate from the filter compartment of the housing 120 to the condensate compartment of the collection jar 140 when the collection jar is attached to the filter housing, as will be discussed in greater detail below.

The respiratory filter and condensate management apparatus 100 may include one or more latch mechanisms 126 for securely and releasably attaching the filter housing 120 to the collection jar 140. For instance, FIG. 2 depicts a pair of latch mechanisms 126 provided on opposite sides of the respiratory filter and condensate management apparatus 100. Each latch mechanism 126 is operable to securely and releasably attach the collection jar 140 to the filter housing 120. As illustrated in FIG. 2, the latch mechanism 126 comprises a lever arm 127, a protrusion or catch 128 extending from the lever arm, and a corresponding receptacle or notch 129 configured to receive a portion of the protrusion or catch 128 in an engaged or locked position. The latch mechanism may include a spring tab, a spring lever, a spring bar, a spring latch, and a snap-fit, among others. The lever arm 127 may include a non-slip gripping surface, such as a textured or roughened surface, among others The lever arm 127 may be pivotably or flexibly connected to the collection jar 140. The receptacle or notch 129 is formed on the filter housing 120. The latch mechanism 126 is operable to lock the collection jar 140 to the filter housing 120 and release the collection jar from the filter housing by respectively engaging and disengaging the catch 128 from the corresponding notch 129. In another implementation, the lever arm may be pivotably or flexibly connected to the filter housing and the receptacle or notch may be formed on the collection jar, such that the latch mechanism is operable to lock the collection jar to the filter housing and release the collection jar from the filter housing by respectively engaging and disengaging a portion of the catch from the corresponding notch.

A filter member 131 is provided within the filter compartment of the housing 120 and is in fluid communication with the air inlet port 122 and the air outlet port 124 for filtering bacteria, viruses, medicament, and/or other waste material exhaled by a patient during respiration. More particularly, the filter member 131 is located in an air flow path from the air inlet port 122 to the air outlet port 124. The filter member 131 may be made from material, such as micro-fiberglass, that is operable to catch bacteria, viruses, medicament, and/or other waste material, while still allowing the flow of air to pass through the filter member. For instance, the filter member 131 may be a high efficiency particulate air (HEPA) filter, or an ultra low particulate air (ULPA) filter, among others. In some implementations, the filter member 131 may be non-pleated, while in other implementations the filter member may be pleated to improve the efficiency of air filtration. The filter member 131 may also be operable to let gaseous vapor comprising small water droplets to pass through. In some aspects, the filter member may be treated with an antimicrobial agent.

Figure 3:
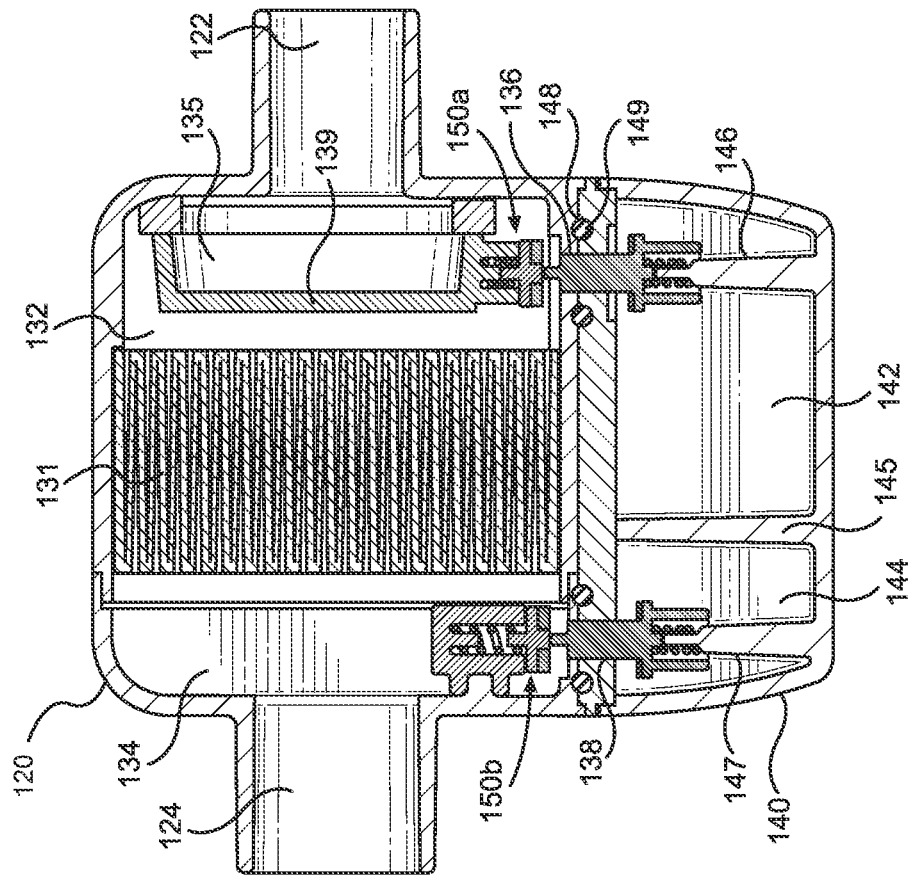
FIG. 3 is a cross-sectional side view of the respiratory filter and condensate management apparatus taken along line 3-3 of FIG. 1.
Figure 6:
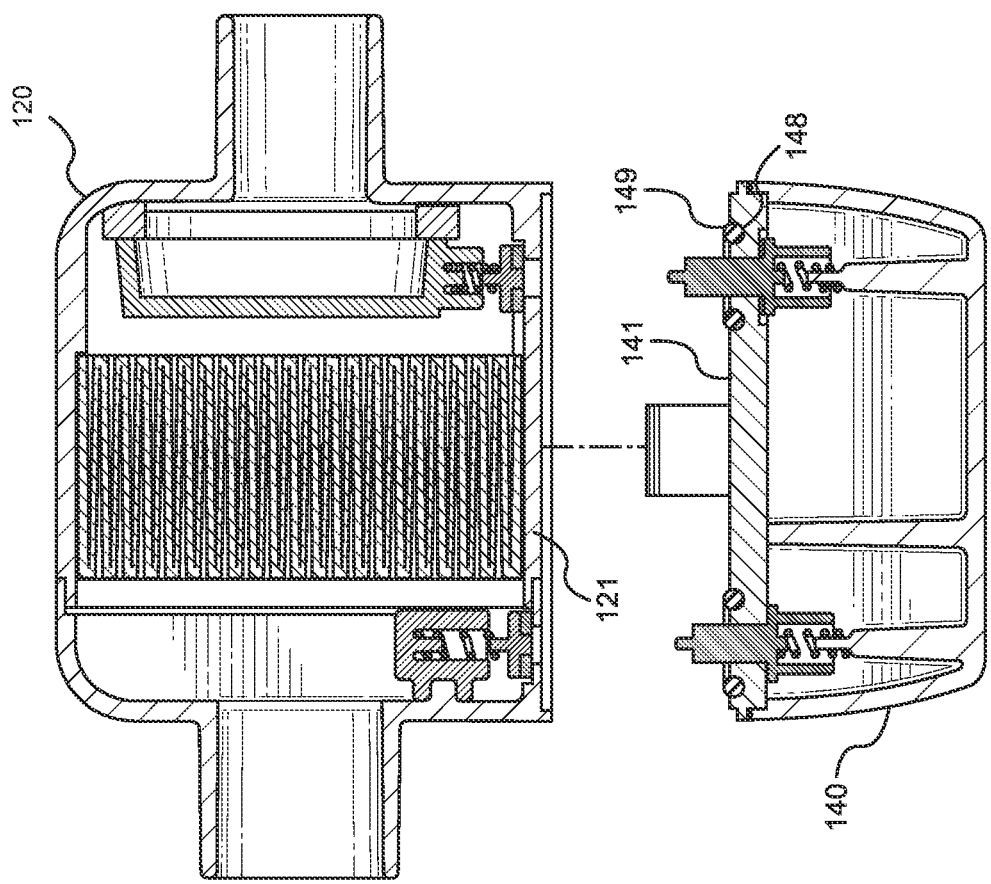
FIG. 6 is a cross-sectional side view of the self-sealing respiratory filter and condensate management apparatus in a detached state.

As shown in FIGS. 2, 3 and 6, the filter member 131 is configured to fit within the filter compartment of the filter housing 120 such that the flow of air from the air inlet port 122 to the air outlet port 124 must pass through the filter member. Stated another way, the filter member 131 has a shape and size relative to a shape and size of the filter compartment of the housing 120 such that the flow of air from the air inlet port 122 to the air outlet port 124 is prevented from bypassing the filter member 131. The filter member 131 may have a generally cuboidal shape, among others.

Heated and humidified air that enters the air inlet port 122 may produce condensate within the filter compartment of the housing 120 due to the presence of colder air within the filter compartment. Condensation or rainout may occur in a patient side 132 of the filter compartment before the air flow passes through the filter member 131, and thus condensate that accumulates within the patient side 132 of the filter compartment may be dirty water. As previously described, the filter member 131 may be operable to let gaseous vapor comprising water droplets pass through. Accordingly, condensation or rainout may also occur in a ventilator side 134 of the filter compartment of the housing after the air flow passes through the filter member 131, and thus condensate that accumulates within the ventilator side 134 of the filter compartment may be clean water.

When the filter housing 120 is attached to the collection jar 140, the condensate compartment is located directly adjacent to and below the filter compartment and is configured to collect liquid water formed by condensation within the filter compartment. In particular, the condensate compartment of the collection jar 140 includes a first reservoir 142 operable to collect liquid formed by condensation within the patient side 132 of the filter compartment, and a second reservoir 144 operable to collect liquid formed by condensation within the ventilator side 134 of the filter compartment. A partition wall 145 may be provided within the condensate compartment between the first and second reservoirs 142, 144 to separate the reservoirs and ensure the dirty water within the first reservoir 142 does not mix with the clean water in the second reservoir 144. The collection jar 140 also includes a cover 141 to prevent liquid from spilling out of the reservoirs when the collection jar is detached from the filter housing.

A pre-filter impact pad 135 may also be provided within the patient side 132 of the filter compartment of the housing 120. The impact pad 135 is operable to remove liquid particles from the humidified flow of air before the humidified air reaches the filter member 131. For instance, such liquid particles removed from the air flow by the impact pad may include medicament particles. As shown in FIGS. 3 and 6, the impact pad 135 is located between the filter member 131 and the air inlet port 122. Thus, the humidified flow of air contacts the impact pad 135 before reaching the filter member 131. The air flow may be diverted around the pad and/or through the pad toward the filter member in order to enhance impaction or catching of aerosol particles.

The impact pad 135 may be absorbent and therefore able to retain the liquid particles. Further, the impact pad may be electrostatically charged for treating the flow of air from the air inlet port 122. For instance, the electrostatic impact pad may comprise a fibrous material imbued with an electrical charge during manufacturing. Thus, the electrostatic impact pad 135 is operable to attract and retain liquid particles in the air flow so as to prevent their further travel into the filter member 131, thus prolonging the lifespan of the filter member.

The impact pad 135 may have generally a planar front surface positioned so as to directly face the air inlet port 122 in a direction perpendicular to the flow of air from the air inlet port 122. Moreover, the impact pad 135 may be shaped and sized such that its cross-section is larger than a cross-section of the air inlet port 122. The impact pad 135 is furthermore located in the direct flow path of air entering through the air inlet port 122. In some aspects the impact pad may have a square or rectangular cross-sectional shape, among others.

The impact pad 135 may be mounted on a mounting frame 139 within the patient side 132 of the filter compartment of the housing 120 so that a clearance surrounding a periphery of the impact pad is formed for allowing the flow of air from the air inlet port to be diverted around the impact pad toward the filter member. The clearance defines a space or gap between the impact pad and an interior surface of the filter housing. The clearance allows the flow of air to be diverted around a top of the pad, a bottom of the pad, and/or the lateral sides of the pad. The impact pad 135 may be secured to the mounting frame 139 by a fastener, such as an adhesive or a clip, among others. According to other aspects, the impact pad may have a conical shape or a cylindrical shape, among others. The mounting frame 139 may also include at least one opening configured to allow the air flow to pass from the air inlet port 122 to the filter member 131 through the impact pad 135.

During use, the electrostatic impact pad 135 causes the air to diffuse, slow down, and be diverted around the pad and/or flow through the pad toward the filter member. The impact pad therefore enhances impaction or catching of aerosol particles. The electrostatic charge on the impact pad 135 attracts liquid particles from the flow of air, thereby preventing the liquid particles from reaching the filter member 131. Accordingly, the electrostatic impact pad is operable to scrub out aerosol from the flow of air from the air inlet port.

During use in patient respiration, liquid condensation that forms within the filter compartment of the housing 120 will drip downward toward the condensate compartment of the collection jar 140 due to the effect of gravity. More specifically, condensate within the patient side 132 of the filter compartment will pass downward through a first condensate or liquid passageway 136 and into the first reservoir 142 of the condensate compartment due to gravity. Similarly, condensate within the ventilator side 134 of the filter compartment will pass downward through a second condensate or liquid passageway 138 and into the second reservoir 144 of the condensate compartment due to gravity.

As depicted in FIG. 3, the first condensate passageway 136 extends through respective portions of the base 121 of the housing, as well as the cover 141 of the collection jar. Likewise, the second condensate passageway 138 extends through other respective portions of the base 121 of the housing and the cover 141 of the collection jar. Each of the first and second condensate passageways 136, 138 are surrounded by a corresponding annular groove 148 formed in an outer surface of the jar cover. Each annular groove 148 is configured to receive a portion of an elastomeric seal 149, such as a rubber O-ring, that provides a fluid tight seal between the housing base 121 and the jar cover 141 when the jar is attached to the housing. A first support member 146, such as a column or pillar, is disposed within the collection jar and is axially aligned with the first condensate passage 136. A second support member 147, such as a column or pillar, is disposed within the collection jar and is axially aligned with the second condensate passage 138.

When the collection jar 140 is attached to the filter housing 120, a patient-side self-closing valve assembly 150a controls the passage of condensate flowing from the patient side 132 of the filter compartment of the housing through the first condensate passageway 136 and into the first reservoir 142 of the condensate compartment of the collection jar. Similarly, when the collection jar 140 is attached to the filter housing 120, a ventilator-side self-closing valve assembly 150b controls the passage of condensate flowing from the ventilator side 134 of the filter compartment of the housing through the second condensate passageway 138 and into the second reservoir 144 of the condensate compartment of the collection jar. Each self-closing valve assembly 150a,b is configured to move to an open position when the filter housing 120 is attached to the collection jar 140, and further configured to move to a closed position when the filter housing is detached from the collection jar, as will be discussed further below.

Figure 4:
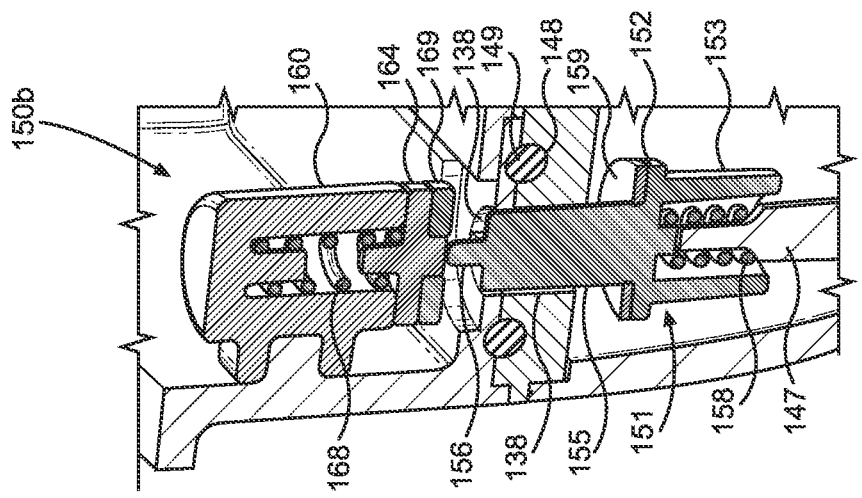
FIG. 4 is a cross-sectional perspective view of a ventilator-side self-closing valve assembly of the respiratory filter and condensate management apparatus in accordance with the present disclosure.

An enlarged view of the ventilator-side self-closing valve assembly 150b is depicted in FIG. 4 for illustration purposes since it should be appreciated that component parts of the patient-side self-closing valve assembly 150a and the ventilator-side self-closing valve assembly 150b are alike. With reference to FIG. 4, the ventilator-side self-closing valve assembly 150b comprises a valve cap 160 and a housing slide 164 that are both disposed within the filter housing. The valve cap 160 may be fixedly secured to the housing or formed integrally with the housing. In some aspects, the patient-side self-closing valve assembly 150a may be fixedly secured to the mounting frame 139 or formed integrally with the mounting frame. In other aspects, the patient-side self-closing valve assembly 150a may be fixedly secured to the housing 120 or formed integrally with the housing.

The valve cap 160 includes a recess configured to receive a housing slide biasing member 168, such as a compression spring. The housing slide biasing member 168 is configured to bias the housing slide 164 toward a closed position in which condensate is prevented from passing through the second condensate passageway 138. In some implementations, the housing slide 164 may include an elastomeric housing seal 169, such as a silicone washer, to ensure a water-tight seal with the base 121 of the housing 120 when in the closed position to prevent condensate from leaking out of the housing through the corresponding condensate passageway.

Figure 5:
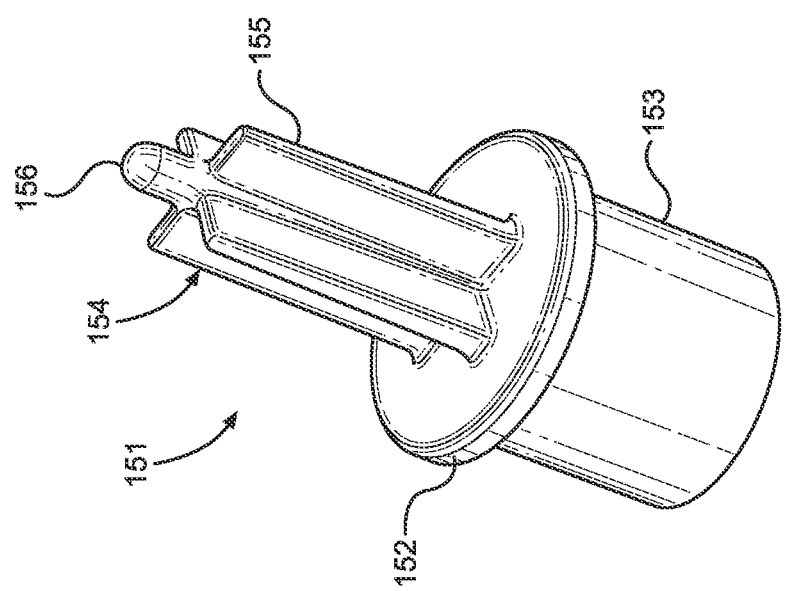
FIG. 5 is a perspective view of a jar slide of the valve assembly in accordance with the present disclosure.

The ventilator-side self-closing valve assembly 150b further comprises a jar slide 151 at least partly disposed within the collection jar 140. As further illustrated in FIG. 5, the jar slide 151 includes a flange 152, which may be annular, among other shapes. A base 153 extends from a first surface of the flange 152, and a valve stem or jar stem 154 extends from a second surface of the flange 152. The valve stem 154 includes at least one vane 155 extending laterally therefrom. As depicted in FIG. 5, the valve stem 154 includes a plurality of vanes 155 extending laterally therefrom. In particular, the valve stem 154 includes four vanes 155 equally spaced apart to form a cross-section shaped as a cross or plus (+) sign. In other implementations, the valve stem may include more or less than four vanes, either equally or not equally spaced apart, and forming other shaped cross-sections. The valve stem 154 further includes a tip 156 configured to abut the housing slide 164 when in the open position.

The base 153 may be cylindrical, among other shapes, and includes a recess configured to receive a jar slide biasing member 158, such as a compression spring. The jar slide 151 is supported by the corresponding support member protruding into the collection jar. For instance, FIG. 4 depicts the jar slide 151 is supported by the second support member 147 protruding into the collection jar. The jar slide biasing member 158 is configured to bias the jar slide 151 toward a closed position in which condensate is prevented from spilling out of the second reservoir 144 through the second condensate passageway 138. In some implementations, the jar slide 151 may include an elastomeric jar seal 159, such as a silicone washer, to ensure a water-tight seal with the cover 141 of the collection jar 140 when in the closed position to prevent condensate from leaking out of the collection jar through the second condensate passageway 138.

In operation, when the collection jar 140 is attached to the filter housing 120, as depicted in FIGS. 3 and 4, the tip 156 of the jar slide 151 contacts the housing slide 164 such that both the jar slide and the housing slide are respectively urged against the biasing force of the jar slide biasing member 158 and the housing slide biasing member 168 toward respective open positions in which liquid condensate is allowed to pass through the corresponding condensate passageway. A channel defined by adjacent vanes 155 of the valve stem 154 allows the condensate to pass through the condensate passageway when the valve stem is inserted into the condensate passageway. Thus, when the collection jar 140 is attached to the filter housing 120, each valve assembly 150a, b automatically assumes the open position to allow condensate to pass from the filter housing through the corresponding condensate passageway and into the collection jar.

When the collection jar 140 is detached from the filter housing 120, as depicted in FIG. 6, the tip 156 of the jar slide 151 no longer contacts the housing slide 164, such that both the jar slide and the housing slide are respectively urged by the biasing force of the jar slide biasing member 158 and the housing slide biasing member 168 toward the closed position in which the corresponding condensate passage is blocked, thus preventing liquid condensate from passing therethrough. As described above, in the closed position, the flange 152 of the jar slide sealingly abuts an interior surface of a portion of the collection jar cover 141 surrounding the corresponding condensate passageway to block it, and thus preventing condensate from spilling out of the collection jar through the condensate passageway. The elastomeric jar seal 159 may be disposed between the flange 152 and the interior surface of the collection jar to ensure a fluid tight seal when the valve assembly is in the closed position.

Similarly, the housing slide 164 sealingly abuts an interior surface of a portion of the filter housing base 121 surrounding the corresponding condensate passageway to block it, and thus preventing condensate from leaking out of the filter housing through the condensate passageway. The elastomeric housing seal 169 may be disposed between the housing slide 164 and the interior surface of the filter housing base to ensure a fluid tight seal. Thus, when the collection jar 140 is detached from the filter housing 120, each valve assembly 150a,b automatically moves to the closed position, thus obstructing the corresponding condensate passageway, and therefore preventing condensate from leaking out of both the filter housing and the collection jar through the corresponding condensate passageway.

FIGS. 7-11 illustrate a self-sealing respiratory filter and condensate management apparatus 200 for a breathing circuit in accordance with another implementation of the present disclosure. The respiratory filter and condensate management apparatus 200 comprises a filter housing 220 and a collection jar 240. The collection jar 240 is releasably attachable to the filter housing 220. The filter housing 220 defines a filter compartment, and the collection jar 240 defines a condensate compartment. The filter housing 220 includes a base 221, an air inlet port 222, and an air outlet port 224. The air inlet port 222 is configured to connect to an expiratory limb of the breathing circuit, and the air outlet port 224 is configured to connect to a ventilator either directly or via a breathing circuit tubing. A self-closing valve assembly 250a,b is provided to regulate passage of condensate from the filter compartment of the housing 220 to the condensate compartment of the collection jar 240 when the collection jar is attached to the filter housing.

The respiratory filter and condensate management apparatus 200 may include one or more latch mechanisms 226 for securely and releasably attaching the filter housing 220 to the collection jar 240. For instance, FIG. 8 depicts a pair of latch mechanisms 226 provided on opposite sides of the respiratory filter and condensate management apparatus 200. Each latch mechanism 226 is operable to securely and releasably attach the collection jar 240 to the filter housing 220. As illustrated in FIG. 8, the latch mechanism 226 comprises a lever arm 227, a protrusion or catch 228 extending from the lever arm, and a corresponding receptacle or notch 229 configured to receive a portion of the protrusion or catch 228 in an engaged or locked position. The latch mechanism may include a spring tab, a spring lever, a spring bar, a spring latch, and a snap-fit, among other configurations. The lever arm 227 may include a non-slip gripping surface, such as a textured or roughened surface, among others.

The lever arm 227 may be pivotably or flexibly connected to the collection jar 240. The receptacle or notch 229 is formed on the filter housing 220. The latch mechanism 226 is operable to lock the collection jar 240 to the filter housing 220 and release the collection jar from the filter housing by respectively engaging and disengaging the catch 228 from the corresponding notch 229. In another implementation, the lever arm may be pivotably or flexibly connected to the filter housing and the receptacle or notch may be formed on the collection jar, such that the latch mechanism is operable to lock the collection jar to the filter housing and release the collection jar from the filter housing by respectively engaging and disengaging a portion of the catch from the corresponding notch.

A filter member 231 is provided within the filter compartment of the housing 220 and is in fluid communication with the air inlet port 222 and the air outlet port 224 for filtering bacteria, viruses, medicament, and/or other waste material exhaled by a patient during respiration. More particularly, the filter member 231 is located in an air flow path from the air inlet port 222 to the air outlet port 224. The filter member 231 may be made from material, such as micro-fiberglass, that is operable to catch bacteria, viruses, medicament, and/or other waste material, while still allowing the flow of air to pass through the filter member. For instance, the filter member 231 may be a high efficiency particulate air (HEPA) filter, or an ultra low particulate air (ULPA) filter, among others. In some implementations, the filter member 231 may be non-pleated, while in other implementations the filter member may be pleated to improve the efficiency of air filtration. The filter member 231 may also be operable to let gaseous vapor comprising small water droplets to pass through. In some aspects, the filter member may be treated with an antimicrobial agent.

Figure 11:
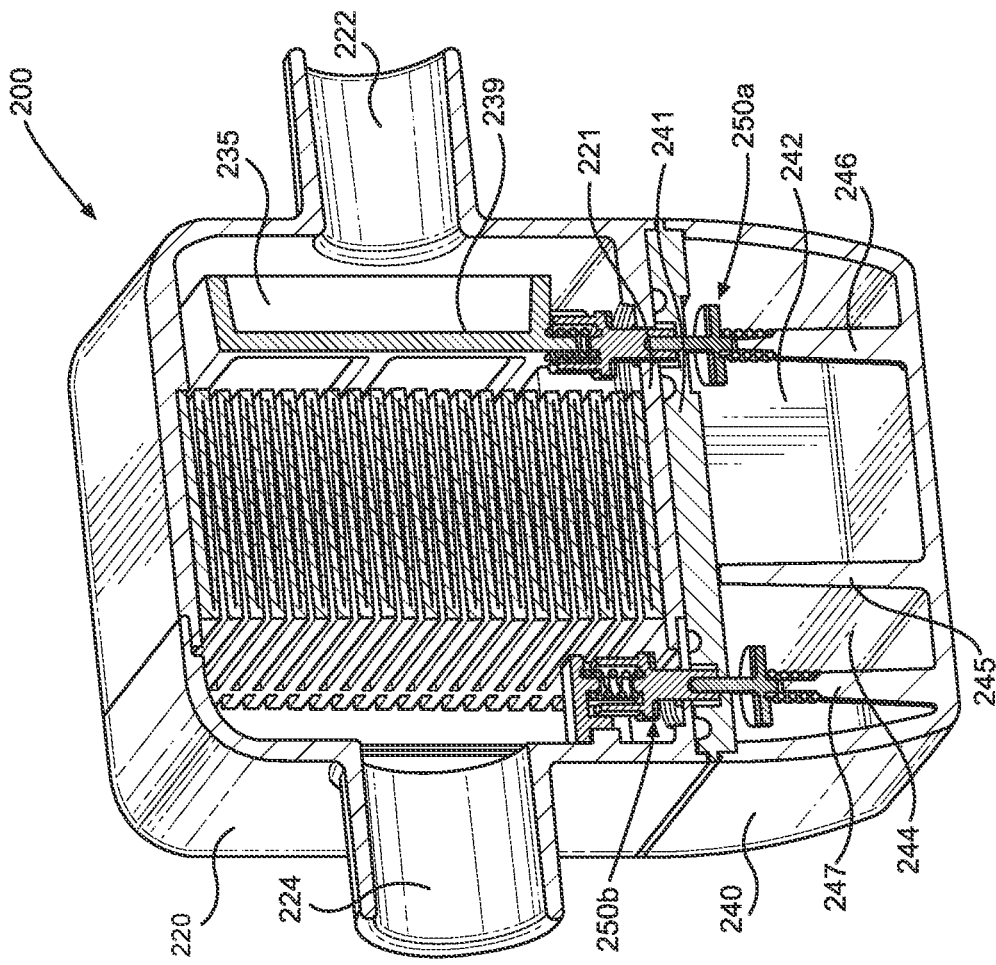
FIG. 11 is a perspective cross-sectional view of the self-sealing respiratory filter and condensate management apparatus of FIG. 9.

As shown in FIGS. 8, 9 and 11, the filter member 231 is configured to fit within the filter compartment of the filter housing 220 such that the flow of air from the air inlet port 222 to the air outlet port 224 must pass through the filter member. Stated another way, the filter member 231 has a shape and size relative to a shape and size of the filter compartment of the housing 220 such that the flow of air from the air inlet port 222 to the air outlet port 224 is prevented from bypassing the filter member 231. The filter member 231 may have a generally cuboidal shape, among others.

Heated and humidified air that enters the air inlet port 222 may produce condensate within the filter compartment of the housing 220 due to the presence of colder air within the filter compartment. Condensation or rainout may occur in a patient side 232 of the filter compartment before the air flow passes through the filter member 231, and thus condensate that accumulates within the patient side 232 of the filter compartment may be dirty water. As previously described, the filter member 231 may be operable to let gaseous vapor comprising water droplets pass through. Accordingly, condensation or rainout may also occur in a ventilator side 234 of the filter compartment of the housing after the air flow passes through the filter member 231, and thus condensate that accumulates within the ventilator side 234 of the filter compartment may be clean water.

When the filter housing 220 is attached to the collection jar 240, the condensate compartment is located directly adjacent to and below the filter compartment and is configured to collect liquid water formed by condensation within the filter compartment. In particular, the condensate compartment of the collection jar 240 includes a first reservoir 242 operable to collect liquid formed by condensation within the patient side 232 of the filter compartment, and a second reservoir 244 operable to collect liquid formed by condensation within the ventilator side 232 of the filter compartment. A partition wall 245 may be provided within the condensate compartment between the first and second reservoirs 242, 244 to separate the reservoirs and ensure the dirty water within the first reservoir 242 does not mix with the clean water in the second reservoir 244. The collection jar 240 also includes a cover 241 to prevent liquid from spilling out of the reservoirs when the collection jar is detached from the filter housing.

A pre-filter impact pad 235 may also be provided within the patient side 232 of the filter compartment of the housing 220. The impact pad 235 is operable to remove liquid particles from the humidified flow of air before the humidified air reaches the filter member 231. For instance, such liquid particles removed from the air flow by the impact pad may include medicament particles. As shown in FIGS. 9 and 11, the impact pad 235 is located between the filter member 231 and the air inlet port 222. Thus, the humidified flow of air contacts the impact pad 235 before reaching the filter member 231. The air flow may be diverted around the pad and/or through the pad toward the filter member in order to enhance impaction or catching of aerosol particles.

The impact pad 235 may be absorbent and therefore able to retain the liquid particles. Further, the impact pad may be electrostatically charged for treating the flow of air from the air inlet port 222. For instance, the electrostatic impact pad may comprise a fibrous material imbued with an electrical charge during manufacturing. Thus, the electrostatic impact pad 235 is operable to attract and retain liquid particles in the air flow so as to prevent their further travel into the filter member 231, thus prolonging the lifespan of the filter member.

The impact pad 235 may have generally a planar front surface positioned so as to directly face the air inlet port 222 in a direction perpendicular to the flow of air from the air inlet port 222. Moreover, the impact pad 235 may be shaped and sized such that its cross-section is larger than a cross-section of the air inlet port 222. The impact pad 235 is furthermore located in the direct flow path of air entering through the air inlet port 222. In some aspects the impact pad may have a square or rectangular cross-sectional shape, among others.

The impact pad 235 may be mounted on a mounting frame 239 within the patient side 232 of the filter compartment of the housing 220 so that a clearance surrounding a periphery of the impact pad is formed for allowing the flow of air from the air inlet port to be diverted around the impact pad toward the filter member. The clearance defines a space or gap between the impact pad and an interior surface of the filter housing. The clearance allows the flow of air to be diverted around a top of the pad, a bottom of the pad, and/or the lateral sides of the pad. The impact pad 235 may be secured to the mounting frame 239 by a fastener, such as an adhesive or a clip, among others. According to other aspects, the impact pad may have a conical shape or a cylindrical shape, among others. The mounting frame 239 may also include at least one opening configured to allow the air flow to pass from the air inlet port 222 to the filter member 231 through the impact pad 235.

Moreover, during use the electrostatic impact pad 235 causes the air to diffuse, slow down, and be diverted around the pad and/or flow through the pad toward the filter member. The impact pad therefore enhances impaction or catching of aerosol particles. The electrostatic charge on the impact pad 235 attracts liquid particles from the flow of air, thereby preventing the liquid particles from reaching the filter member 231. Accordingly, the electrostatic impact pad is operable to scrub out aerosol from the flow of air from the air inlet port.

During use in patient respiration, liquid condensation that forms within the filter compartment of the housing 220 will drip downward toward the condensate compartment of the collection jar 240 due to the effect of gravity. More specifically, condensate within the patient side 232 of the filter compartment will pass downward through a first condensate or liquid passageway 236 and into the first reservoir 242 of the condensate compartment due to gravity. Similarly, condensate within the ventilator side 234 of the filter compartment will pass downward through a second condensate or liquid passageway 238 and into the second reservoir 244 of the condensate compartment due to gravity.

The first condensate passageway 236 extends through respective portions of the base 221 of the housing and the cover 241 of the collection jar. Likewise, the second condensate passageway 238 extends through other respective portions of the base 221 of the housing and the cover 241 of the collection jar. In some aspects, one or more apertures 223 may be provided in the filter housing base 221 and configured to provide fluid communication between the filter compartment and the corresponding condensate passage when the respective valve assembly is in the open position. Similarly, one or more apertures 243 may be provided in the jar cover 241 and configured to provide fluid communication between the condensate collection compartment and the corresponding condensate passage when the respective valve assembly is in the open position.

Each of the first and second condensate passageways 236, 238 are surrounded by a corresponding annular groove 248 formed in an outer surface of the jar cover. Each annular groove 248 is configured to receive a portion of an elastomeric seal 249, such as a rubber O-ring, that provides a fluid tight seal between the housing base 221 and the jar cover 241 when the jar is attached to the housing. A first support member 246, such as a column or pillar, is disposed within the collection jar and is axially aligned with the first condensate passage 236. A second support member 247, such as a column or pillar, is disposed within the collection jar and is axially aligned with the second condensate passage 238.

When the collection jar 240 is attached to the filter housing 220, a patient-side self-closing valve assembly 250a controls the passage of condensate flowing from the patient side 232 of the filter compartment of the housing through the first condensate passageway 236 and into the first reservoir 242 of the condensate compartment of the collection jar. Similarly, when the collection jar 240 is attached to the filter housing 220, a ventilator-side self-closing valve assembly 250b controls the passage of condensate flowing from the ventilator side 234 of the filter compartment of the housing through the second condensate passageway 238 and into the second reservoir 244 of the condensate compartment of the collection jar. Each self-closing valve assembly 250a,b is configured to move to an open position when the filter housing 220 is attached to the collection jar 240, and further configured to move to a closed position when the filter housing is detached from the collection jar, as will be discussed further below.

Figure 10B:
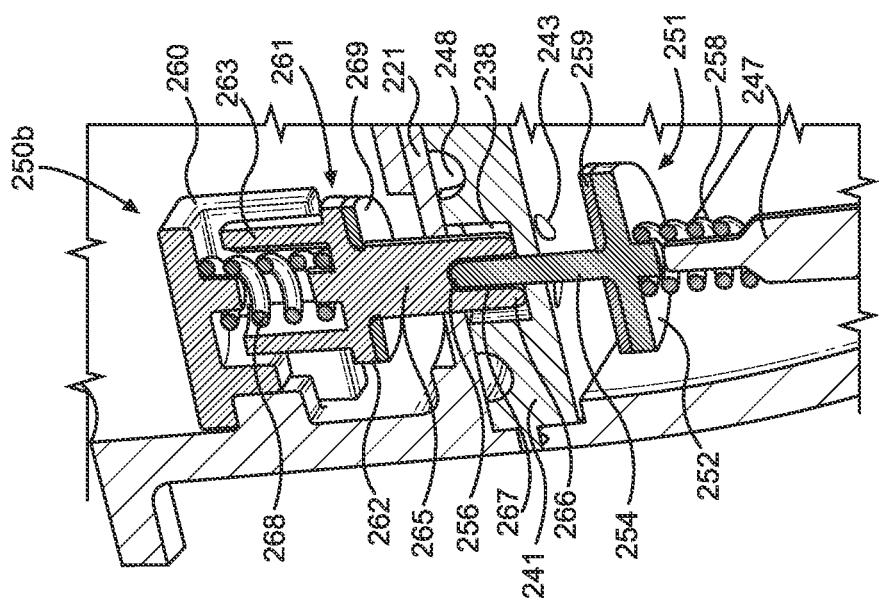
FIG. 10*b* is a partial cross-sectional bottom perspective view of the ventilator-side valve assembly of the respiratory filter and condensate management apparatus of FIG. 9.

An enlarged view of the ventilator-side self-closing valve assembly 250b is depicted in FIGS. 10a and 10b for illustration purposes since it should be appreciated that component parts of the patient-side self-closing valve assembly 250a and the ventilator-side self-closing valve assembly 250b are alike. The ventilator-side self-closing valve assembly 250b comprises a valve cap 260 and a housing slide 261 that are both disposed within the filter housing. The valve cap 260 may be fixedly secured to the housing or formed integrally with the housing. In some aspects, the patient-side self-closing valve assembly 250a may be fixedly secured to the mounting frame 239 or formed integrally with the mounting frame. In other aspects, the patient-side self-closing valve assembly 250a may be fixedly secured to the housing 220 or formed integrally with the housing.

The jar slide 251 includes a flange 252, which may be annular, among other shapes. A valve stem or jar stem 254 extends from a surface of the flange 252 and includes a tip 256 configured to abut the housing slide 261 when in the open position. The flange 252 is configured to abut a jar slide biasing member 258, such as a compression spring. The jar slide 251 is supported by the corresponding support member protruding into the collection jar. For instance, FIGS. 10a and 10b depict the jar slide 251 is supported by the second support member 247 protruding into the collection jar. The jar slide biasing member 258 is configured to bias the jar slide 251 toward a closed position in which condensate is prevented from spilling out of the second reservoir 244 through the second condensate passageway 238. In some implementations, the jar slide 251 may include an elastomeric jar seal 259, such as a silicone washer, to ensure a water-tight seal over the at least one aperture 243 in the jar cover 241 when in the closed position to prevent condensate from leaking out of the collection jar through the second condensate passageway 238.

The housing slide 261 includes a flange 262, which may be annular, among other shapes. A base 263 extends from a first surface of the flange 262, and a housing stem 265 extends from a second surface of the flange 262. The housing stem 265 includes a tip 266 having a recess 267 configured to receive and abut the jar slide tip 256 when in the open position. The base 263 may be cylindrical, among other shapes, and includes a recess configured to receive a housing slide biasing member 268, such as a compression spring. The valve cap 260 includes a recess configured to receive base 263 and the housing slide biasing member 268. The housing slide biasing member 268 is configured to bias the housing slide 261 toward a closed position in which condensate is prevented from passing through the second condensate passageway 238. In some implementations, the housing slide 261 may include an elastomeric housing seal 269, such as a silicone washer, to ensure a water-tight seal over the at least one aperture 223 in the housing base 221 when in the closed position to prevent condensate from leaking out of the housing through the second condensate passageway 238.

In operation, when the collection jar 240 is attached to the filter housing 220, the tip 256 of the jar slide 251 contacts the housing slide 261 such that both the jar slide and the housing slide are respectively urged against the biasing force of the jar slide biasing member 258 and the housing slide biasing member 268 toward an open position in which liquid condensate is allowed to pass through the corresponding condensate passageway via the respective apertures 223, 243. Thus, when the collection jar 240 is attached to the filter housing 220, each valve assembly 250a, b automatically moves to the open position to allow condensate to pass from the filter housing through the corresponding condensate passageway and into the collection jar.

When the collection jar 240 is detached from the filter housing 220, the tip 256 of the jar slide 251 no longer contacts the housing slide 261 such that both the jar slide and the housing slide are respectively urged by the biasing force of the jar slide biasing member 258 and the housing slide biasing member 268 toward the closed position in which the at least one aperture 223, 243 of the corresponding condensate passage is blocked, thus preventing liquid from passing therethrough.

Stated another way, in the closed position, the flange 252 of the jar slide sealingly covers the at least one aperture 243 in the jar cover 241 to block the corresponding condensate passageway and thus prevent condensate from spilling out of the collection jar through the condensate passageway. The elastomeric jar seal 259 may be disposed between the flange 252 and the interior surface of the collection jar to ensure a fluid tight seal when the valve assembly is in the closed position. Similarly, the housing slide 261 sealingly covers the at least one aperture 223 in the filter housing base 221 to block the corresponding condensate passageway and thus prevent condensate from leaking out of the filter housing through the condensate passageway. The elastomeric housing seal 269 may be disposed between the flange 262 of the housing slide and the interior surface of the filter housing base to ensure a fluid tight seal. Thus, when the collection jar 240 is detached from the filter housing 220, each valve assembly 250a,b automatically moves to the closed position to obstruct the corresponding condensate passageway, and therefore prevent condensate from leaking out of both the filter housing and the collection jar through the corresponding condensate passageway.

FIGS. 12-16 illustrate a self-sealing respiratory filter and condensate management apparatus 300 for a breathing circuit in accordance with another implementation of the present disclosure. The respiratory filter and condensate management apparatus 300 comprises a filter housing 320 and a collection jar 340. The collection jar 340 is releasably attachable to the filter housing 320. The filter housing 320 defines a filter compartment, and the collection jar 340 defines a condensate compartment. The filter housing 320 includes a base 321, an air inlet port 322, and an air outlet port 324. The air inlet port 322 is configured to connect to an expiratory limb of the breathing circuit, and the air outlet port 324 is configured to connect to a ventilator either directly or via a breathing circuit tube. A self-closing valve assembly 350a,b is provided to regulate passage of condensate from the filter compartment of the housing 320 to the condensate compartment of the collection jar 340 when the collection jar is attached to the filter housing.

The respiratory filter and condensate management apparatus 300 may include one or more latch mechanisms 326 for securely and releasably attaching the filter housing 320 to the collection jar 340. For instance, a pair of latch mechanisms 326 may be provided on opposite sides of the respiratory filter and condensate management apparatus 300. Each latch mechanism 326 is operable to securely and releasably attach the collection jar 340 to the filter housing 320. As illustrated in FIG. 13, the latch mechanism 326 comprises a lever arm 327, a protrusion or catch 328 extending from the lever arm, and a corresponding receptacle or notch 329 configured to receive a portion of the protrusion or catch 328 in an engaged or locked position. The latch mechanism may include a spring tab, a spring lever, a spring bar, a spring latch, and a snap-fit, among other configurations. The lever arm 327 may include a non-slip gripping surface, such as a textured or roughened surface, among others.

In the implementation shown in FIG. 13, the lever arm 327 is pivotably or flexibly connected to the collection jar 340, and the receptacle or notch 329 is formed on the filter housing 320. The latch mechanism 326 is operable to lock the collection jar 340 to the filter housing 320 and release the collection jar from the filter housing by respectively engaging and disengaging the catch 328 from the corresponding notch 329. In another implementation, the lever arm may be pivotably or flexibly connected to the filter housing and the receptacle or notch may be formed on the collection jar, such that the latch mechanism is operable to lock the collection jar to the filter housing and release the collection jar from the filter housing by respectively engaging and disengaging a portion of the catch from the corresponding notch.

A filter member 331 is provided within the filter compartment of the housing 320 and is in fluid communication with the air inlet port 322 and the air outlet port 324 for filtering bacteria, viruses, medicament, and/or other waste material exhaled by a patient during respiration. More particularly, the filter member 331 is located in an air flow path from the air inlet port 322 to the air outlet port 324. The filter member 331 may be made from material, such as micro-fiberglass, that is operable to catch bacteria, viruses, medicament, and/or other waste material, while still allowing the flow of air to pass through the filter member. For instance, the filter member 331 may be a high efficiency particulate air (HEPA) filter, or an ultra low particulate air (ULPA) filter, among others. In some implementations, the filter member 331 may be non-pleated, while in other implementations the filter member may be pleated to improve the efficiency of air filtration. The filter member 331 may also be operable to let gaseous vapor comprising small water droplets to pass through. In some aspects, the filter member may be treated with an antimicrobial agent.

Figure 14:
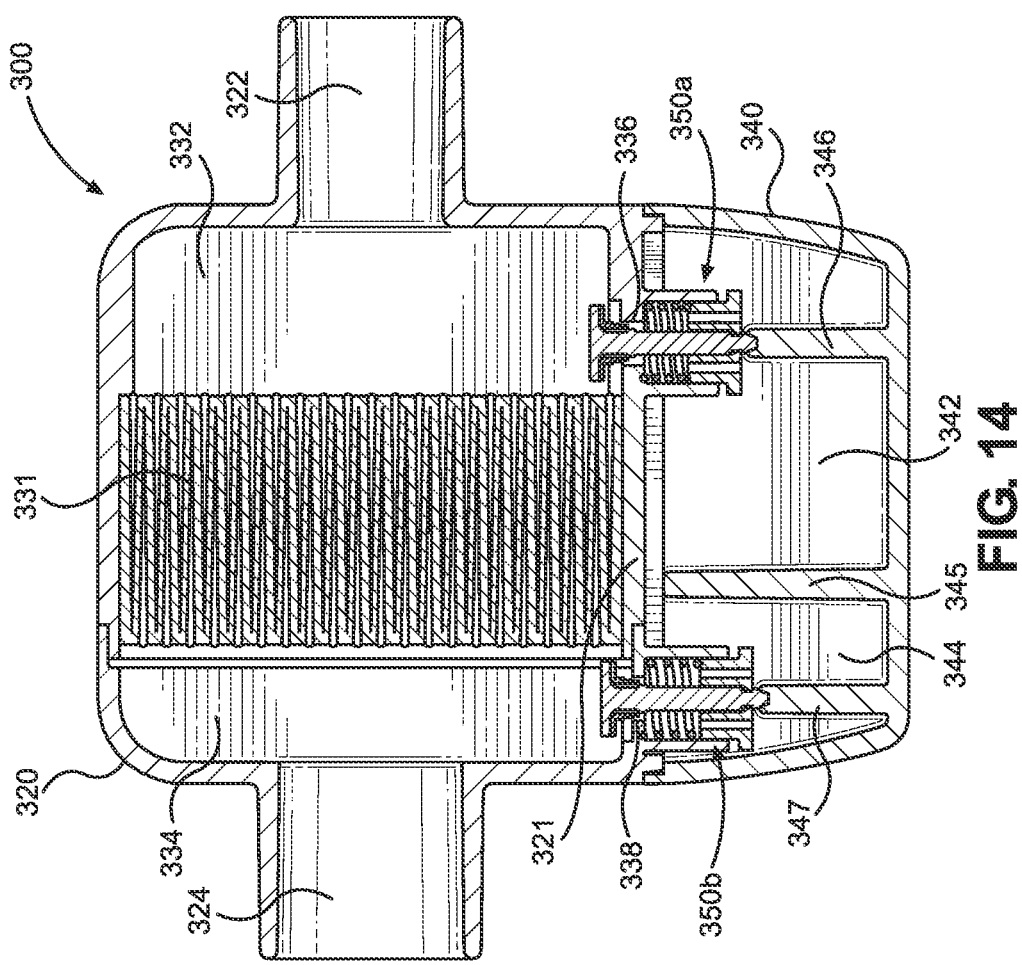
FIG. 14 is a cross-sectional view from a front of the apparatus depicted in FIG. 12.
Figure 16:
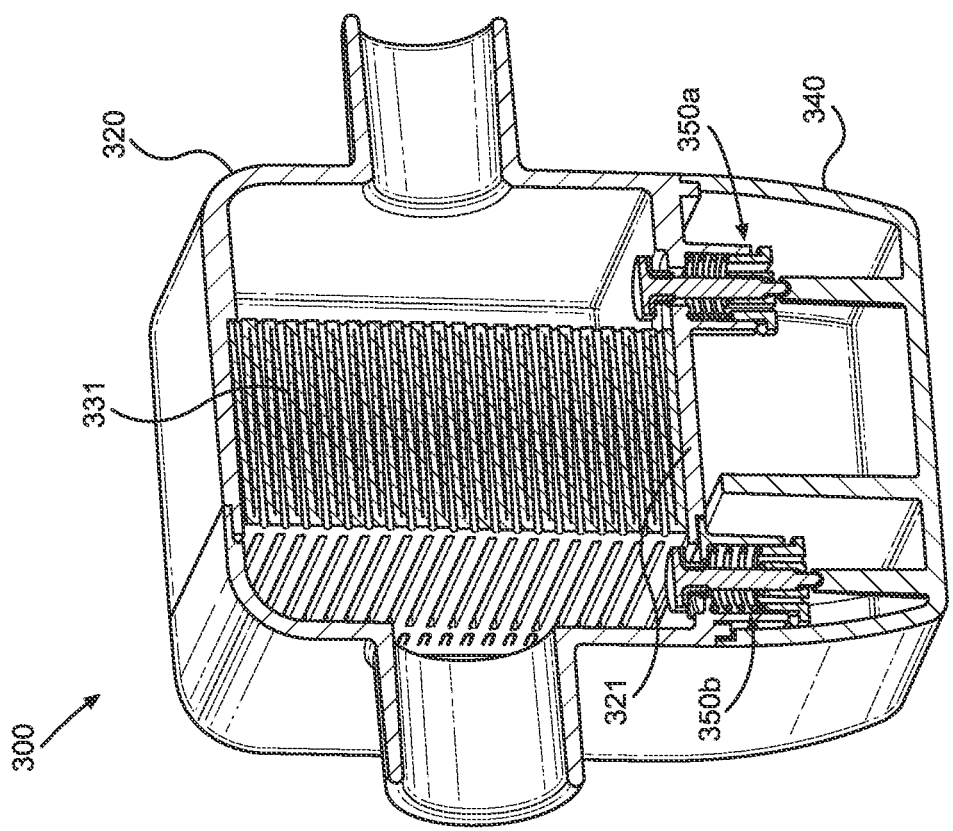
FIG. 16 is a cross-sectional perspective view of the apparatus depicted in FIG. 14.

As shown in FIGS. 13, 14 and 16, the filter member 331 is configured to fit within the filter compartment of the filter housing 320 such that the flow of air from the air inlet port 322 to the air outlet port 324 must pass through the filter member. Stated another way, the filter member 331 has a shape and size relative to a shape and size of the filter compartment of the housing 320 such that the flow of air from the air inlet port 322 to the air outlet port 324 is prevented from bypassing the filter member 331. The filter member 331 may have a generally cuboidal shape, among others.

Heated and humidified air that enters the air inlet port 322 may produce condensate within the filter compartment of the housing 320 due to the presence of colder air within the filter compartment. Condensation or rainout may occur in a patient side 332 of the filter compartment before the air flow passes through the filter member 331, and thus condensate that accumulates within the patient side 332 of the filter compartment may be dirty water. As previously described, the filter member 331 may be operable to let gaseous vapor comprising water droplets pass through. Accordingly, condensation or rainout may also occur in a ventilator side 334 of the filter compartment of the housing after the air flow passes through the filter member 331, and thus condensate that accumulates within the ventilator side 334 of the filter compartment may be clean water.

When the filter housing 320 is attached to the collection jar 340, the condensate compartment is located directly adjacent to and below the filter compartment and is configured to collect liquid water formed by condensation within the filter compartment. In particular, the condensate compartment of the collection jar 340 includes a first reservoir 342 operable to collect liquid formed by condensation within the patient side 332 of the filter compartment, and a second reservoir 344 operable to collect liquid formed by condensation within the ventilator side 332 of the filter compartment. A partition wall 345 may be provided within the condensate compartment between the first and second reservoirs 342, 344 to separate the reservoirs and ensure the dirty water within the first reservoir 342 does not mix with the clean water in the second reservoir 344.

Figure 15:
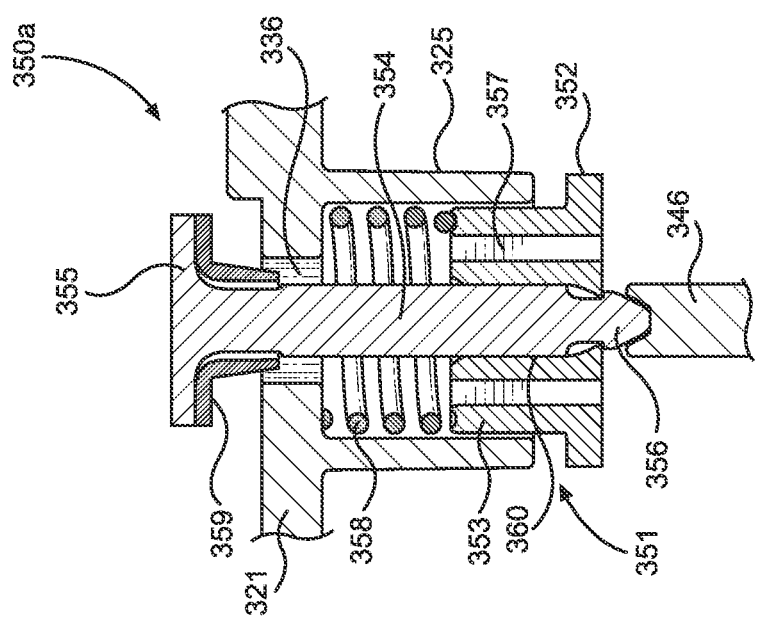
FIG. 15 is a partial cross-sectional view of a self-sealing valve assembly of the apparatus depicted in FIG. 14.

During use in patient respiration, liquid condensation that forms within the filter compartment of the housing 320 will drip downward toward the condensate compartment of the collection jar 340 due to the effect of gravity. More specifically, condensate within the patient side 332 of the filter compartment will pass downward through a first condensate or liquid passageway 336 and into the first reservoir 342 of the condensate compartment due to gravity. Similarly, condensate within the ventilator side 334 of the filter compartment will pass downward through a second condensate or liquid passageway 338 and into the second reservoir 344 of the condensate compartment due to gravity. As depicted in FIG. 15, the first condensate passageway 336 extends through the base 321 of the housing. Likewise, the second condensate passageway 338 extends through the base 321 of the housing. A first support member 346, such as a column or pillar, is disposed within the collection jar and is axially aligned with the first condensate passage 336. A second support member 347, such as a column or pillar, is disposed within the collection jar and is axially aligned with the second condensate passage 338.

When the collection jar 340 is attached to the filter housing 320, a patient-side self-closing valve assembly 350a controls the passage of condensate flowing from the patient side 332 of the filter compartment of the housing through the first condensate passageway 336 and into the first reservoir 342 of the condensate compartment of the collection jar. Similarly, when the collection jar 340 is attached to the filter housing 320, a ventilator-side self-closing valve assembly 350b controls the passage of condensate flowing from the ventilator side 334 of the filter compartment of the housing through the second condensate passageway 338 and into the second reservoir 344 of the condensate compartment of the collection jar. Each self-closing valve assembly 350a,b is configured to be in an open position when the filter housing 320 is attached to the collection jar 340, and further configured to be in a closed position when the filter housing is detached from the collection jar.

When the collection jar 340 is attached to the filter housing 320, a first self-closing valve assembly 250a controls the passage of condensate flowing from the patient side 332 of the filter compartment 330 through the first condensate passageway 336 and into the first reservoir 342 of the condensate compartment. An enlarged view of the patient-side self-closing valve assembly 350a is depicted in FIG. 15 for illustration purposes since it should be appreciated that component parts of the patient-side self-closing valve assembly 350a and the ventilator-side self-closing valve assembly 350b are alike.

The valve assembly 350a includes a jar slide 351 comprising a base 353 attached to a valve stem or jar stem 354. The valve stem 354 includes a proximal end having an enlarged valve head 355, and a distal end having a valve tip 356. A distal end of the base 353 includes a flange 352, which may be annular, among other shapes. The base 353 also includes at least one longitudinal valve slot 357 configured to allow liquid condensate to pass therethrough when the valve assembly is in the open position. A valve wall 325 protrudes from a bottom surface of the base 321 of the filter housing. The valve wall 325 may be cylindrical, among other shapes, and defines a recess configured to receive a jar slide biasing member 358 and a portion of the base 353 of the jar slide. The jar slide biasing member 358, such as a compression spring, is disposed between the base 321 of the housing and the base 353 of the jar slide. The base 353 of the jar slide also includes a central longitudinal through-hole 360 in which a portion of the valve stem 354 is received. The tip 356 of the valve stem protrudes from the distal end of the base 353 of the jar slide and is operable to abut the corresponding support member protruding into the collection jar.

In FIG. 15, for instance, the valve tip 356 abuts the first support member 346 protruding into the collection jar when the valve assembly 350a is in an open position. The valve head 355 at the proximal end of the valve stem is configured to allow condensate to pass through the corresponding condensate passageway in the base 321 of the housing when the valve assembly is in the open position. Further, the valve head 355 is configured to block condensate from passing through the corresponding condensate passageway in the base 321 of the housing when the valve assembly is in the closed position. In some implementations, the jar slide 351 may include an elastomeric jar seal 359, such as a silicone washer, to ensure a water-tight seal between the valve head 355 the corresponding condensate passageway when in the closed position to prevent condensate from leaking out of the housing 320.

The valve tip 356 extends past a surface of the flange 352 and is operable to abut the corresponding support member 346 when in the open position. The base 353 is configured to abut the jar slide biasing member 358 such that the jar slide biasing member 358 is operable to bias the jar slide 351 toward a closed position in which condensate is prevented from dripping out of the housing 320 through the respective condensate passageway. Thus, in operation, when the collection jar 340 is attached to the filter housing 320, the valve tip 356 of the jar slide 351 contacts the corresponding support member 346, 347 such that the jar slide 351 is urged against the biasing force of the jar slide biasing member 358 toward an open position in which liquid condensate is allowed to pass through the corresponding condensate passageways 336, 338. Accordingly, when the collection jar 340 is attached to the filter housing 320, each valve assembly 350a,b automatically moves to the open position to allow condensate to pass from the filter housing through the corresponding condensate passageway and into the collection jar.

When the collection jar 340 is detached from the filter housing 320, the valve tip 356 no longer contacts the corresponding support member, such that the jar slide 351 is urged by the biasing force of the jar slide biasing member 358 toward the closed position in which the corresponding condensate passage is blocked, thus preventing liquid condensate from passing therethrough. Stated another way, in the closed position, the enlarged valve head 355 sealingly covers the corresponding condensate passageway in the base 321 of the housing 320 to block the passageway, and thus prevent condensate from dripping out of the filter housing. Accordingly, when the collection jar 340 is detached from the filter housing 320, each valve assembly 350a,b automatically moves to the closed position to obstruct the corresponding condensate passageway, and therefore prevent condensate from leaking out of the filter housing through the corresponding condensate passageway.

Figure 17:
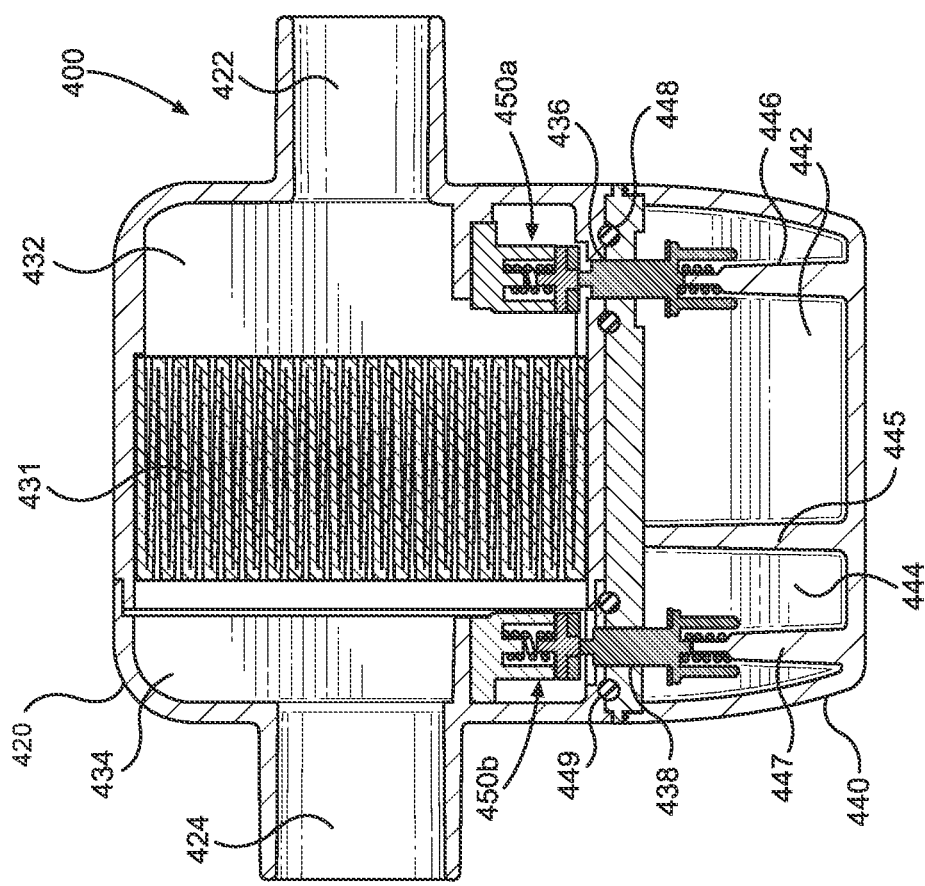
FIG. 17 is a cross-sectional view of a self-sealing respiratory filter and condensate management apparatus in an attached state according to another implementation of the present disclosure.
Figure 18:
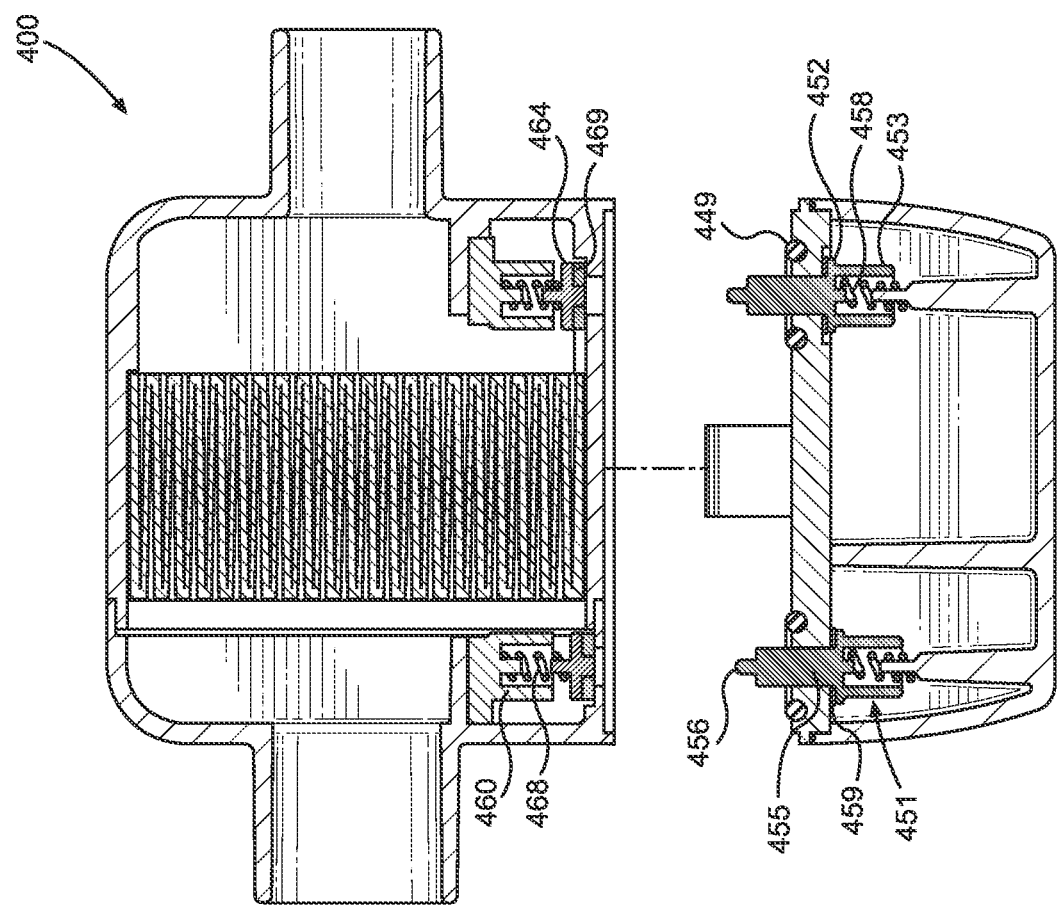
FIG. 18 is a cross-sectional view of the self-sealing respiratory filter and condensate management apparatus of FIG. 17 in a detached state.

FIGS. 17 and 18 illustrate a self-sealing respiratory filter and condensate management apparatus 400 for a breathing circuit in accordance with another implementation of the present disclosure. Similar to the apparatus 100 discussed in detail above, the respiratory filter and condensate management apparatus 400 comprises a filter housing 420 and a collection jar 440. The collection jar 440 is releasably attachable to the filter housing 420. The filter housing 420 defines a filter compartment, and the collection jar 440 defines a condensate compartment. The filter housing 420 includes base 421, an air inlet port 422, and an air outlet port 424. The air inlet port 422 is configured to connect to an expiratory limb of the breathing circuit, and the air outlet port 424 is configured to connect to a ventilator either directly or via a breathing circuit tubing. A self-closing valve assembly 450a, b is provided to regulate passage of condensate from the filter compartment of the housing 420 to the condensate compartment of the collection jar 440 when the collection jar is attached to the filter housing.

The respiratory filter and condensate management apparatus 400 may include one or more latch mechanisms comprising one or more components or characteristics of any of the other latch mechanisms previously described above for securely and releasably attaching the filter housing 420 to the collection jar 440.

A filter member 431 is provided within the filter compartment of the housing 420 and is in fluid communication with the air inlet port 422 and the air outlet port 424 for filtering bacteria, viruses, medicament, and/or other waste material exhaled by a patient during respiration. The filter member 431 may comprise one or more components or characteristics of any of the other filter members previously described above.

Heated and humidified air that enters the air inlet port 422 may produce condensate within the filter compartment of the housing 420 due to the presence of colder air within the filter compartment. Condensation or rainout may occur in a patient side 432 of the filter compartment before the air flow passes through the filter member 431, and thus condensate that accumulates within the patient side 432 of the filter compartment may be dirty water. As previously described, the filter member 431 may be operable to let gaseous vapor comprising water droplets pass through. Accordingly, condensation or rainout may also occur in a ventilator side 434 of the filter compartment of the housing after the air flow passes through the filter member 431, and thus condensate that accumulates within the ventilator side 434 of the filter compartment may be clean water.

When the filter housing 420 is attached to the collection jar 440, the condensate compartment is located directly adjacent to and below the filter compartment and is configured to collect liquid water formed by condensation within the filter compartment. In particular, the condensate compartment of the collection jar 440 includes a first reservoir 442 operable to collect liquid formed by condensation within the patient side 432 of the filter compartment, and a second reservoir 444 operable to collect liquid formed by condensation within the ventilator side 434 of the filter compartment. A partition wall 445 may be provided within the condensate compartment between the first and second reservoirs 442, 444 to separate the reservoirs and ensure the dirty water within the first reservoir 442 does not mix with the clean water in the second reservoir 444. The collection jar 440 also includes a cover 441 to prevent liquid from spilling out of the reservoirs when the collection jar is detached from the filter housing.

During use in patient respiration, liquid condensation that forms within the filter compartment of the housing 420 will drip downward toward the condensate compartment of the collection jar 440 due to the effect of gravity. More specifically, condensate within the patient side 432 of the filter compartment will pass downward through a first condensate or liquid passageway 436 and into the first reservoir 442 of the condensate compartment due to gravity. Similarly, condensate within the ventilator side 434 of the filter compartment will pass downward through a second condensate or liquid passageway 438 and into the second reservoir 444 of the condensate compartment due to gravity.

The first condensate passageway 436 extends through respective portions of the base 421 of the housing, as well as the cover 441 of the collection jar. Likewise, the second condensate passageway 438 extends through other respective portions of the base 421 of the housing and the cover 441 of the collection jar. Each of the first and second condensate passageways 436, 438 are surrounded by a corresponding annular groove 448 formed in an outer surface of the jar cover. Each annular groove 448 is configured to receive a portion of an elastomeric seal 449, such as a rubber O-ring, that provides a fluid tight seal between the housing base 421 and the jar cover 441 when the jar is attached to the housing. A first support member 446, such as a column or pillar, is disposed within the collection jar and is axially aligned with the first condensate passage 436. A second support member 447, such as a column or pillar, is disposed within the collection jar and is axially aligned with the second condensate passage 438.

When the collection jar 440 is attached to the filter housing 420, as shown in FIG. 17, a patient-side self-closing valve assembly 450a controls the passage of condensate flowing from the patient side 432 of the filter compartment of the housing through the first condensate passageway 436 and into the first reservoir 442 of the condensate compartment of the collection jar. Similarly, when the collection jar 440 is attached to the filter housing 420, a ventilator-side self-closing valve assembly 450b controls the passage of condensate flowing from the ventilator side 434 of the filter compartment of the housing through the second condensate passageway 438 and into the second reservoir 444 of the condensate compartment of the collection jar. Each self-closing valve assembly 450a,b is configured to move to an open position when the filter housing 420 is attached to the collection jar 440, and further configured to move to a closed position when the filter housing is detached from the collection jar.

Each self-closing valve assembly 450a,b may comprise one or more components or characteristics of any of the other self-closing valve assemblies previously described above. In particular, the ventilator-side self-closing valve assembly 450b comprises a valve cap 460 and a housing slide 464 that are both disposed within the filter housing. The valve cap 460 may be fixedly secured to the housing or formed integrally with the housing. In some aspects, the patient-side self-closing valve assembly 450a may similarly be fixedly secured to the housing or formed integrally with the mounting frame.

The valve cap 460 includes a recess configured to receive a housing slide biasing member 468, such as a compression spring. The housing slide biasing member 468 is configured to bias the housing slide 464 toward a closed position in which condensate is prevented from passing through the second condensate passageway 438. In some implementations, the housing slide 464 may include an elastomeric housing seal 469, such as a silicone washer, to ensure a water-tight seal with the base 421 of the housing 420 when in the closed position to prevent condensate from leaking out of the housing through the corresponding condensate passageway.

The ventilator-side self-closing valve assembly 450b further comprises a jar slide 451 at least partly disposed within the collection jar 440. The jar slide 451 includes a flange 452, which may be annular, among other shapes. A base 453 extends from a first surface of the flange 452, and a valve stem or jar stem extends from a second surface of the flange 452. The valve stem includes at least one vane 455 extending laterally therefrom. The valve stem may include a plurality of vanes 455 extending laterally therefrom. The valve stem further includes a tip 456 configured to abut the housing slide 464 when in the open position, as shown in FIG. 17.

The base 453 may be cylindrical, among other shapes, and includes a recess configured to receive a jar slide biasing member 458, such as a compression spring. The jar slide 451 is supported by the corresponding support member protruding into the collection jar. The jar slide biasing member 458 is configured to bias the jar slide 451 toward a closed position in which condensate is prevented from spilling out of the second reservoir 444 through the second condensate passageway 438. In some implementations, the jar slide 451 may include an elastomeric jar seal 459, such as a silicone washer, to ensure a water-tight seal with the cover 441 of the collection jar 440 when in the closed position to prevent condensate from leaking out of the collection jar through the second condensate passageway 438.

In operation, when the collection jar 440 is attached to the filter housing 420, as depicted in FIG. 17, the tip 456 of the jar slide 451 contacts the housing slide 464 such that both the jar slide and the housing slide are respectively urged against the biasing force of the jar slide biasing member 458 and the housing slide biasing member 468 toward respective open positions in which liquid condensate is allowed to pass through the corresponding condensate passageway. A channel defined by adjacent vanes 455 of the valve stem allows the condensate to pass through the condensate passageway when the valve stem is inserted into the condensate passageway. Thus, when the collection jar 440 is attached to the filter housing 420, each valve assembly 450a,b automatically assumes the open position to allow condensate to pass from the filter housing through the corresponding condensate passageway and into the collection jar.

When the collection jar 440 is detached from the filter housing 420, as depicted in FIG. 18, the tip 456 of the jar slide 451 no longer contacts the housing slide 464, such that both the jar slide and the housing slide are respectively urged by the biasing force of the jar slide biasing member 458 and the housing slide biasing member 468 toward the closed position in which the corresponding condensate passage is blocked, thus preventing liquid condensate from passing therethrough. As described above, in the closed position, the flange 452 of the jar slide sealingly abuts an interior surface of a portion of the collection jar cover 441 surrounding the corresponding condensate passageway to block it, and thus preventing condensate from spilling out of the collection jar through the condensate passageway. The elastomeric jar seal 459 may be disposed between the flange 452 and the interior surface of the collection jar to ensure a fluid tight seal when the valve assembly is in the closed position.

Similarly, the housing slide 464 sealingly abuts an interior surface of a portion of the filter housing base 421 surrounding the corresponding condensate passageway to block it, and thus preventing condensate from leaking out of the filter housing through the condensate passageway. The elastomeric housing seal 469 may be disposed between the housing slide 464 and the interior surface of the filter housing base to ensure a fluid tight seal. Thus, when the collection jar 440 is detached from the filter housing 420, each valve assembly 450a,b automatically moves to the closed position, thus obstructing the corresponding condensate passageway, and therefore preventing condensate from leaking out of both the filter housing and the collection jar through the corresponding condensate passageway.

In each of the above implementations of the respiratory filter and condensate management apparatus, a user is able to detach the collection jar from the filter housing when the user wants to empty the condensate collected within the reservoirs. Upon such detachment, the self-sealing valve assemblies automatically close to prevent accidental spillage of condensate.

While the respiratory filter and condensate management apparatus has been described in terms of what may be considered to be specific aspects, the present disclosure is not limited to the disclosed aspects. Additional modifications and improvements to the respiratory filter and condensate management apparatus may be apparent to those skilled in the art. Moreover, the many features and advantages of the disclosure are apparent from the detailed specification, and thus, it is intended by the appended claims to cover all such features and advantages of the disclosure which fall within the spirit and scope of the disclosure.

Further, it is not desired to limit the disclosure to the exact construction and operation illustrated and described, and accordingly, all suitable modifications and equivalents may be resorted to, falling within the scope of the disclosure. The present disclosure should therefore be considered as illustrative and not restrictive. As such, this disclosure is intended to cover various modifications and similar arrangements included within the spirit and scope of the claims, which should be accorded their broadest interpretation so as to encompass all such modifications and similar structures.

What is claimed is:

1. A respiratory filter and condensate management apparatus for a breathing circuit, the apparatus comprising:
    a filter housing including an air inlet port, an air outlet port, a base, and a base drain passing through the base, the air inlet port configured to receive a flow of expiratory air, and the air outlet port configured to output the flow of expiratory air;
    a filter member provided within the filter housing and located in a flow path of the expiratory air between the air inlet port and the air outlet port;
    a collection jar removably attached to the filter housing, the collection jar including a liquid reservoir, a spill cover fixedly secured to the collection jar, and a cover drain passing through the spill cover, the cover drain and the base drain forming a liquid passageway operable to provide fluid communication between the filter housing and the liquid reservoir when the collection jar is attached to the filter housing, and the liquid reservoir operable to collect liquid formed by condensation in the flow of expiratory air within the filter housing when the collection jar is attached to the filter housing; and
    a valve assembly configured to permit passage of the liquid formed by condensation in the flow of expiratory gas through the liquid passageway when the valve assembly is in an open position, and configured to prevent passage of the liquid through the liquid passageway when the valve assembly is in a closed position.

2. The respiratory filter and condensate management apparatus according to claim 1, wherein the valve assembly is operable to automatically assume the open position when the filter housing is attached to the collection jar.

3. The respiratory filter and condensate management apparatus according to claim 1, wherein the valve assembly is operable to automatically assume the closed position when the filter housing is detached from the collection jar.

4. The respiratory filter and condensate management apparatus according to claim 1, wherein the valve assembly comprises a housing slide configured to close the base drain of the filter housing when the collection jar is detached from the filter housing.

5. The respiratory filter and condensate management apparatus according to claim 4, wherein the valve assembly further comprises a housing slide biasing member configured to bias the housing slide toward the base drain.

6. The respiratory filter and condensate management apparatus according to claim 5, wherein the valve assembly further comprises an elastomeric housing seal to provide a water-tight seal between the housing slide and the base drain when the valve assembly is in the closed position.

7. The respiratory filter and condensate management apparatus according to claim 1, wherein the valve assembly comprises a jar slide configured to close the cover drain of the collection jar when the collection jar is detached from the filter housing.

8. The respiratory filter and condensate management apparatus according to claim 7, wherein the valve assembly further comprises a jar slide biasing member configured to bias the jar slide toward the cover drain.

9. The respiratory filter and condensate management apparatus according to claim 8, wherein the valve assembly further comprises an elastomeric jar seal to provide a water-tight seal between the jar slide and the cover drain when the valve assembly is in the closed position.

10. The respiratory filter and condensate management apparatus according to claim 1, further comprising a latch mechanism configured to securely and releasably attach the filter housing to the collection jar.

11. The respiratory filter and condensate management apparatus according to claim 10, wherein the latch mechanism is operable to permit detachment of the collection jar from the filter housing without disconnecting the filter housing from the breathing circuit.

12. The respiratory filter and condensate management apparatus according to claim 1, further comprising an impact pad provided within the filter housing and operable to remove liquid from the flow of expiratory air.

13. The respiratory filter and condensate management apparatus according to claim 12, wherein the impact pad is an electrostatic pad.

14. The respiratory filter and condensate management apparatus according to claim 1, wherein the filter member is pleated.

15. A respiratory filter and condensate management apparatus for a breathing circuit, the apparatus comprising:
   a filter housing including a patient end and a ventilator end, the patient end having an air inlet port configured to receive a flow of expiratory air, and the ventilator end having an air outlet port configured to output the flow of expiratory air;
   a filter member provided within the filter housing and located in a flow path of the expiratory air between the air inlet port and the air outlet port;
   a collection jar removably attached to the filter housing, the collection jar including a patient end liquid reservoir operable to collect liquid formed by condensation in the flow of expiratory air within the filter housing when the collection jar is attached to the filter housing;
   a spill cover fixedly secured to the collection jar; and
   a patient end valve assembly configured to move to an open position when the filter housing is attached to the collection jar, and further configured to move to a closed position when the filter housing is detached from the collection jar.

16. The respiratory filter and condensate management apparatus according to claim 15, wherein the filter housing further includes a base having a patient end base drain.

17. The respiratory filter and condensate management apparatus according to claim 16, wherein the spill cover includes a patient end cover drain, the patient end cover drain and the patient end base drain forming a patient end liquid passageway operable to provide fluid communication between the filter housing and the patient end liquid reservoir when the collection jar is attached to the filter housing.

18. The respiratory filter and condensate management apparatus according to claim 17, wherein the patient end valve assembly is further configured to permit passage of the liquid formed by condensation in the flow of expiratory gas through the patient end liquid passageway when the patient end valve assembly is in an open position, and further configured to prevent passage of the liquid through the patient end liquid passageway when the patient end valve assembly is in a closed position.

19. The respiratory filter and condensate management apparatus according to claim 15, wherein the collection jar further includes a ventilator end liquid reservoir operable to collect liquid formed by condensation in the flow of expiratory air within the filter housing when the collection jar is attached to the filter housing.

20. The respiratory filter and condensate management apparatus according to claim 19, further comprising a ventilator end valve assembly configured to move to an open position when the filter housing is attached to the collection jar, and further configured to move to a closed position when the filter housing is detached from the collection jar.

* * * * *